(12) United States Patent
Berlia et al.

(10) Patent No.: US 11,992,558 B2
(45) Date of Patent: May 28, 2024

(54) CONTROLLED RELEASE FORMULATION COMPRISING FLAVOXATE

(71) Applicant: Sushma Paul Berlia, New Delhi (IN)

(72) Inventors: Sushma Paul Berlia, New Delhi (IN); Nishant Berlia, New Delhi (IN); Anupama Diwan, Haryana (IN); Sunder Singh Bhandari, Uttar Pradesh (IN)

(73) Assignee: Sushma Paul Berlia, New Delhi (IN)

( * ) Notice: Subject to any disclaimer, the term of this patent is extended or adjusted under 35 U.S.C. 154(b) by 260 days.

(21) Appl. No.: 17/261,858

(22) PCT Filed: Jul. 21, 2019

(86) PCT No.: PCT/IB2019/056223
§ 371 (c)(1),
(2) Date: Jan. 20, 2021

(87) PCT Pub. No.: WO2020/021422
PCT Pub. Date: Jan. 30, 2020

(65) Prior Publication Data
US 2021/0299053 A1    Sep. 30, 2021

(30) Foreign Application Priority Data

Jul. 21, 2018 (IN) .............................. 201811027281

(51) Int. Cl.
| | | |
|---|---|---|
| *A61K 9/20* | (2006.01) | |
| *A61J 3/10* | (2006.01) | |
| *A61K 9/00* | (2006.01) | |
| *A61K 9/28* | (2006.01) | |
| *A61K 31/453* | (2006.01) | |

(52) U.S. Cl.
CPC ............... *A61K 9/2077* (2013.01); *A61J 3/10* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2095* (2013.01); *A61K 9/2853* (2013.01); *A61K 9/2893* (2013.01); *A61K 31/453* (2013.01)

(58) Field of Classification Search
CPC .. A61K 9/2077; A61K 9/0053; A61K 9/2009; A61K 9/2013; A61J 3/10
See application file for complete search history.

(56) References Cited

U.S. PATENT DOCUMENTS

| | | | | |
|---|---|---|---|---|
| 5,165,937 | A * | 11/1992 | Santus et al. .......... | A01N 43/40 424/468 |
| 5,328,903 | A * | 7/1994 | Ishii et al. ........... | A61K 31/595 514/168 |
| 9,642,809 | B2 * | 5/2017 | Hemmingsen et al. . | A61K 9/20 |
| 9,750,701 | B2 * | 9/2017 | Jans et al. ............... | A61K 9/20 |

FOREIGN PATENT DOCUMENTS

| | | |
|---|---|---|
| EP | 0393572 A2 | 10/1990 |
| EP | 0250374 B1 | 5/1991 |
| JP | S63154619 A | 6/1988 |

OTHER PUBLICATIONS

Shyamala. J. K—Formulation Design, Development and Invitro Evaluation of Abacavir Sulphate Gastroretentive Microspheres—J. K.K. Nattaraja College of Pharmacy Kumarapalayam—638183 Tamilnadu.—REG.No. 261510262 (Year: 2017).*
Niijima M, et al. A multicenter clinical trial of flavoxate hydrochloride. Nishinippon Hinyokika 1981; 43: 1055-1063.
Recordati Pharmaceuticals Limited, Urispas 200 mg Film-coated Tablets—Summary of Product Characteristics, Nov. 30, 2018, p. 3.
Ruffman R. A review of flavoxate hydrochloride in the treatment of urge incontinence. J. Int Med Res. Sep. 1988-Oct. 16(5):317-30.
Satyavathi K, et al. Formulation and development of Flavoxate hydrochloride extended release capsules. IJPSR (2014) vol. 5 (5), 1949-56.
Zor M, et al. Flavoxate in urogynecology: An old drug revisited. Int Urogynecol J. Jul. 2014; 26(7): 959-66.

* cited by examiner

*Primary Examiner* — Robert A Wax
*Assistant Examiner* — Andre Mach
(74) *Attorney, Agent, or Firm* — FINNEGAN, HENDERSON, FARABOW, GARRETT & DUNNER, LLP

(57) ABSTRACT

The present invention relates to a controlled release oral formulation comprising about 400 mg to about 800 mg of flavoxate salt as an active ingredient, suitable polymers, binders, and excipients, and lacking an acidifying agent. The present invention also provides a method of preparing the controlled release oral formulation of about 400 mg to 800 mg of flavoxate salt. The controlled release formulation of present invention may comprise micronized particles of drug. The controlled release formulation has a controlled release profile of up to 24 hours, that is pH independent, and that is alcohol dose dumping risk-free.

30 Claims, 12 Drawing Sheets

| Time in hrs | % Drug Released |
|---|---|
| 0 | 0 |
| 2 | 22.45 |
| 3 | 28.44 |
| 4 | 34.66 |
| 5 | 49.24 |
| 6 | 58.33 |
| 7 | 62.21 |
| 8 | 71.92 |
| 9 | 74.39 |
| 10 | 77.97 |
| 12 | 83.89 |
| 14 | 88.78 |
| 16 | 91.94 |
| 24 | 99.99 |

| Time in hrs | % Drug Released |
|---|---|
| 0 | 0 |
| 1 | 18.68 |
| 2 | 26.7 |
| 3 | 33.11 |
| 4 | 41.95 |
| 5 | 52.82 |
| 6 | 63.73 |
| 7 | 73.35 |
| 8 | 80.22 |
| 10 | 89.26 |
| 12 | 93.25 |
| 14 | 94.17 |
| 16 | 99.31 |
| 24 | 99.31 |

| Time in hrs | % Drug Released |
|---|---|
| 0 | 0 |
| 2 | 11.68 |
| 4 | 31.47 |
| 6 | 53 |
| 8 | 68.59 |
| 10 | 81.63 |
| 12 | 87.24 |
| 14 | 89.4 |
| 16 | 92.66 |
| 18 | 93.61 |
| 20 | 95.38 |
| 24 | 99.9 |

| Time in hrs | % Drug Released |
|---|---|
| 0 | 0 |
| 1 | 19.05 |
| 2 | 29.12 |
| 3 | 40.93 |
| 4 | 45.62 |
| 5 | 57.91 |
| 6 | 67.15 |
| 7 | 70.61 |
| 8 | 77.01 |
| 10 | 82.51 |
| 12 | 88.32 |
| 14 | 91.09 |
| 16 | 93.29 |
| 18 | 95.91 |
| 20 | 97.49 |
| 22 | 98.84 |
| 24 | 99.3 |

| Time in hrs | % Drug Released |
|---|---|
| 0 | 0 |
| 1 | 11 |
| 2 | 19 |
| 3 | 26 |
| 4 | 35 |
| 5 | 42 |
| 6 | 51 |
| 7 | 58 |
| 8 | 67 |
| 10 | 80 |
| 12 | 91 |
| 14 | 98 |
| 16 | 99 |
| 18 | 101 |
| 20 | 102 |
| 22 | 103 |
| 24 | 103 |

| Time in hrs | % Drug Released |
|---|---|
| 0 | 0 |
| 1 | 13.5 |
| 2 | 23.4 |
| 3 | 30.5 |
| 4 | 38.9 |
| 5 | 45.6 |
| 6 | 58.9 |
| 7 | 65.4 |
| 8 | 70.5 |
| 10 | 74.7 |
| 12 | 81.2 |
| 14 | 87.9 |
| 16 | 91.9 |
| 18 | 95.0 |
| 20 | 99.9 |

| Time in hrs | % Drug Released |
|---|---|
| 0 | 0 |
| 1 | 7.87 |
| 2 | 17.62 |
| 3 | 25.66 |
| 4 | 34.04 |
| 5 | 42.91 |
| 6 | 55.26 |
| 7 | 63.14 |
| 8 | 68.51 |
| 10 | 76.7 |
| 12 | 80.88 |
| 14 | 89.85 |
| 16 | 92.06 |
| 18 | 93.39 |
| 20 | 96.52 |

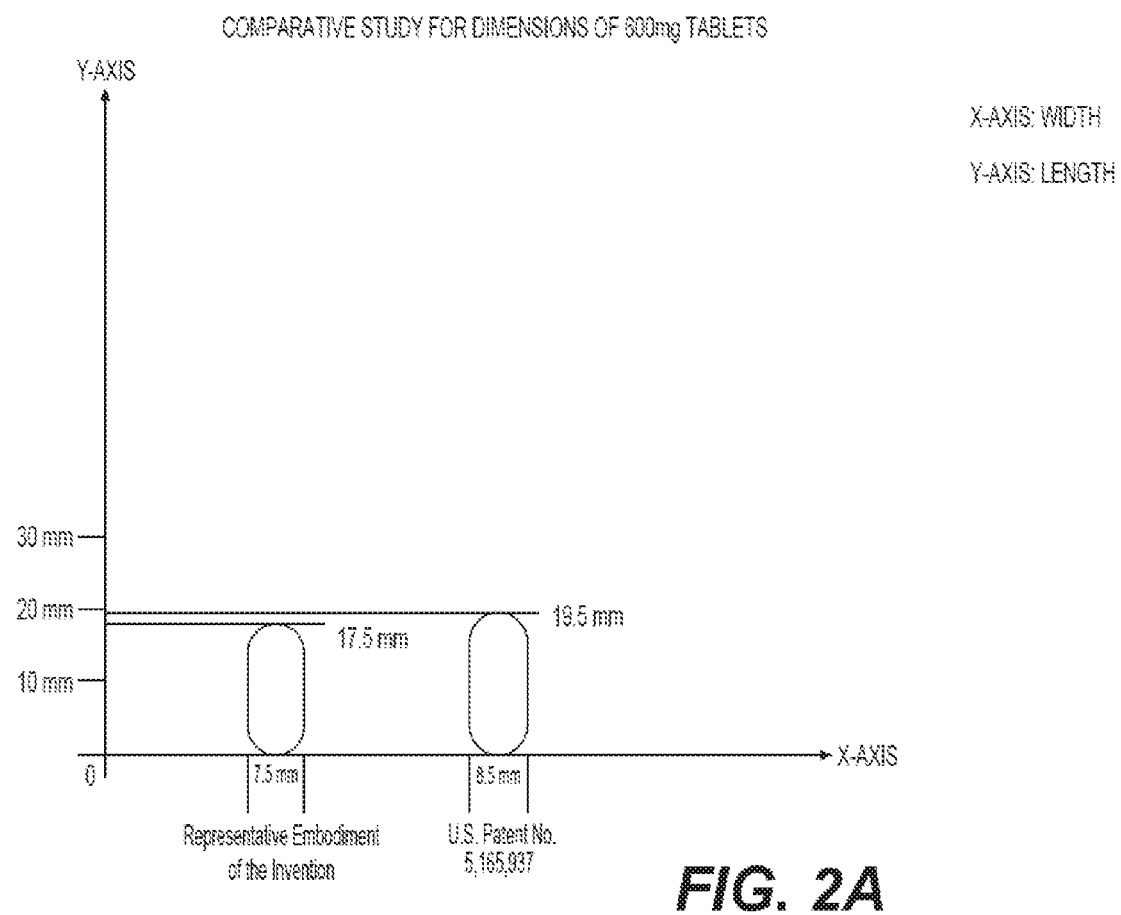

Diamond: Embodiment with colloidal silicon dioxide
Square: Embodiment without colloidal silicon dioxide Diamond: Embodiment with PVP K30 as binder
Square: Embodiment with PVA as binder Diamond: 0% Alcohol
Square: 40% Alcohol Diamond: 0% Alcohol
Square: 40% Alcohol Diamond: Embodiment of Present Invention (Exp-P2)
Square: Embodiment of US Patent No. 5,165,937 (FT-03)

Diamond: pH 1.2
Square: pH 7.4

Diamond: pH 1.2
Square: pH 7.4

Diamond: pH 1.2
Square: pH 7.4

Diamond: pH 1.2
Square: pH 7.4

Diamond: pH 1.2
Square: pH 7.4

Diamond: pH 1.2
Square: pH 7.4

CONTROLLED RELEASE FORMULATION COMPRISING FLAVOXATE

This application is a national stage application under 35 U.S.C. § 371 of International Patent Application No. PCT/162019/056223, filed Jul. 21, 2019, which designated the U.S. and claims priority from Indian Provisional Application No. 201811027281, filed Jul. 21, 2018, which are both hereby incorporated by reference in their entireties.

FIELD OF THE INVENTION

The present invention relates to a controlled release formulation of a lipophilic acid soluble drug. The controlled release formulation is a sub-gram formulation which contains a high dose of the lipophilic drug. The formulation of the present invention provides a drug release of up to 24 hours. The present invention particularly relates to a controlled release formulation of flavoxate hydrochloride (2-piperidinoethyl-3-methylflavone 8-carboxylate hydrochloride). The formulation enables incorporation of up to 800 mg of flavoxate into a sub-gram tablet for its oral delivery. The composition also enables a single-dosage treatment regimen for patients, which may improve patient compliance and quality of life.

BACKGROUND OF THE INVENTION

Oral ingestion is the most convenient and commonly employed route of drug delivery due to its ease of administration, high patient compliance, cost effectiveness, reduced sterility constraints, and flexibility in the design of dosage form.

However, the major challenge with oral dosage forms lies in their poor bioavailability. The oral bioavailability depends on several factors including aqueous solubility, drug permeability, dissolution rate, first-pass metabolism, pre-systemic metabolism, and susceptibility to efflux mechanisms. The most frequent causes of low oral bioavailability are attributed to poor solubility and low permeability.

Solubility plays a major role for other dosage forms. Solubility is one of the important parameters to achieve a desired concentration of drug in systemic circulation for achieving a required (therapeutic) pharmacological response. Poorly water-soluble drugs often require high doses in order to reach therapeutic plasma concentrations after oral administration. Low aqueous solubility is the major problem encountered with formulation development of drugs. For any drug to be absorbed, it must be present in the form of an aqueous solution at the site of absorption. Water is the solvent of choice for liquid pharmaceutical formulations. Most of the drugs having poor aqueous solubility are either weakly acidic or weakly basic. 2-piperidinoethyl 3-methylflavone-8-carboxylate hydrochloride (hereinafter referred to as flavoxate or flavoxate hydrochloride) is a spasmolytic drug with potent smooth muscle relaxant properties. It inhibits the phosphodiesterase enzyme and, by calcium antagonistic action, relaxes smooth muscle. The drug acts preferentially on the genitourinary tract and has been used therapeutically for symptomatic relief of pollakiuria, particularly nocturia, dysuria, urgency, vesicle suprapubic pain, frequency, and urinary incontinence originating from various pathological situations such as prostatitis, urethritis, cystitis, urethero-cystitis, uretherotrigonitis, and the side effects of radiotherapy or surgical therapy of the urinary tract. In addition, flavoxate is indicated for the relief of vesico-urethral spasm due to catheterization, cystoscopy, or indwelling catheter, prior to cystoscopy or catheterization, or sequelae of surgical intervention of the lower urinary tract. Flavoxate is also used to relieve irritative symptoms of benign prostatic hyperplasia (BPH) and overactive bladder. Flavoxate is a flavonic derivative and commercially available in 100 mg or 200 mg as immediate release tablets, because the typical therapeutic dosage requirement of flavoxate is 600 to 800 mg/day, or up to 1200 mg/day, multiple doses must be administered each day.

Oral studies in man have indicated that flavoxate is readily absorbed from the intestine and converted, to a large extent, almost immediately to 3-methylflavone-8-carboxylic acid (MFCA) [Zor et al. Flavoxate in urogynecology: an old drug revisited. Int Urogynecol J. 2015 July; 26(7): 959-66]. Both MFCA and flavoxate inhibit cAMP-dependent phosphodiesterase, which is crucial for smooth muscle relaxation. Its half-life at 100 mg equivalent administered intravenously was determined to be 83.3 minutes and apparent volume of distribution 2.89 l/kg. No free flavoxate was found in urine (24 hours). However, 47% of the dose was excreted as MFCA. The peak level of MFCA was attained at 30-60 mins after oral administration of 200 mg dose and at around two hours following the 400 mg dose. About 50% of the dose was excreted as MFCA within 12 hours; most being excreted within the first 6 hours (Recordati Pharmaceuticals Limited, Urispas 200 mg Film-coated Tablets—Summary of Product Characteristics, Nov. 30, 2018, p. 3; Ruffmann R. A review of flavoxate hydrochloride in the treatment of urge incontinence. J. Int Med Res. 1988 September-October; 16(5):317-30). With a short half-life, the duration of its therapeutic activity is about 5 to 6 hours making it impossible for patients to ingest a dosage sufficient enough to provide longer therapeutic coverage which is at least for the duration of an overnight sleep. Due to its short half-life, maintaining effective therapeutic levels (at least 1 µg/ml) of the drug in circulation remains a challenge. Furthermore, poor aqueous solubility of flavoxate presents formulation problems due to their slow rate of dissolution.

In 2005, several drugs were either withdrawn from the market or had their warning labels enhanced because of the effects of ethanol on the controlled release compositions of the drug. FDA (Food and Drug Administration) has also indicated that for all future sustained release products, in vitro testing for alcohol-induced undermining of sustained release characteristics may be advisable as a routine characterization test. It is thus required to evaluate all types of CR (Controlled Release) formulations for the risk of unexpected drug release from the formulation. If ADD (Alcohol Dose Dumping) is observed or suspected, the product needs to be reformulated.

Thus, there is a requirement in the art for oral formulation of flavoxate with controlled release of drug, in sufficient quantity, for sufficient duration of time and free of ADD risk. Such a formulation would provide many advantages over conventional immediate release tablets. Some of the aided advantages would be enhanced patient compliance; reduction in dosing frequency; diminished in vivo fluctuation of drug concentrations; maintenance of drug concentrations in a desired range; and abridged side effects from immediate release of drug.

A formulation able to extend the therapeutic window offering a high dosage of flavoxate as a single-dose drug would reduce the frequency of administration, and thereby considerably improve compliance as well as the quality of life of the patient. This is especially important considering that therapy using flavoxate is typically long term and is often administered to elderly patients who have a much more difficult time navigating repeated nocturnal risings. Pills, tablets, or capsules are the preferred form of drug, and administration of one tablet per day providing an effective plasma concentration of drug for 24 hours would be ideal.

The current commercially available treatment regimen with flavoxate requires administering the drug three to four times at dosages of 100 mg or 200 mg QID (quater in die or four times a day). At these low dosages, the therapeutic window is small, perhaps requiring hourly intake to keep the circulating plasma concentration at the required 1 microgram per milliliter level for therapeutic efficacy. Lower dosages also carry the risk of poor patient compliance, for instance, when an elderly sufferer forgets to take the tablet regularly, or the more serious risk of over-dosing by forgetfully consuming one or more tablets superfluously. Nocturia is a frequently overlooked situation of poor sleep in the elderly. Conventional, immediate release flavoxate taken in the evening may not be able to cover the entire duration of sleep, causing bothersome symptoms of nocturia.

Drugs may be released at once (immediate release) or they may be released intermittently in pulsatile fashion, or they may be released in a controlled manner (controlled release) where the drug is released in the body over an extended period of time (e.g., over many hours, or one day). It has been noted that, the absorption rate of flavoxate decreases with increased dosage; hence dose dumping should be avoided. Dose dumping is a phenomenon of drug metabolism in which inter alia environmental factors and/or physiological factors can cause the premature and/or exaggerated release of a drug. This can greatly increase the concentration of a drug in the body and thereby produce adverse effects or even drug-induced toxicity. Thus a controlled release of flavoxate is needed which avoids any such dose dumping in the patient's body. From a controlled release formulation standpoint, out of 600 mg or 800 mg flavoxate OD drug, sufficient quantity of drug is released instantly, attaining minimum effective concentration (MEC) of MFCA above 1 µg/ml and further release is such that MEC is maintained for an effective 24 hours. The half-life of MFCA is known to be short viz. t½ of 3.5 hrs. (Ruffmann R. A review of flavoxate hydrochloride in the treatment of urge incontinence. J Int Med Res. 1988 September-October; 16(5):317-30).

Additionally, flavoxate hydrochloride is known to have low compressibility and poor flow properties. Its poor compressibility makes molding flavoxate into compact, orally administered tablets a challenge. With drugs exhibiting poor compressibility, maintaining suitable tablet size and physical properties such as sufficient tablet hardness and appropriate friability is important.

There is no account in the pharmaceutical literature of a compressed tablet of flavoxate or a salt thereof formulated as a single-dose tablet and capable of providing 24 hour therapeutic coverage. To accommodate the required 600/800 mg flavoxate in a tablet-ingestible form, the amount of controlled release polymers, binders, and excipients has to be kept so low that the final overall weight of the tablet does not exceed the limit of practicality. Very large, non-chewable tablets cannot be ingested easily by the elderly, much less by one in a weakened physical condition. Thus, small and non-bulky oral tablets are another goal for formulation of controlled release oral formulation of flavoxate for meeting patient compliance.

Japanese Patent Application No. JP 63-154619 and European Patent Application EP 250374 have attempted to address the problem of administering flavoxate hydrochloride employing delayed-release formulations. The Japanese patent application describes an extended release formulation by preparing a fast dissolving flavoxate preparation and a slow dissolving flavoxate preparation and blending them in a 1:0.5 ratio to achieve release over twice the duration obtained by a 100 mg flavoxate made by traditional (immediate release) methods. However, even by applying the teachings of these two patent applications, it has not been possible to provide 24 hour efficacy or to obtain pharmaceutical formulations that can be administered in a single dosage form when the dosage of the active ingredient is very large. U.S. Pat. No. 9,750,701 on the other hand, teaches achieving retarded release profiles of drugs such as flavoxate by rendering anisotropic physical properties to tablets through providing indentations in the tablets.

Satyavathi et al. in I. J. Pharma. Sci. & Res. (2014) 5 (5), 1949-56; describes making extended release capsules of flavoxate using ethyl cellulose and hydroxypropyl methyl cellulose, extruding them as pellets, drug-loading the pellets, and providing extended release coating on the drug-laden pellets. Dissolution profiles show that about 70% of the drug was released by the second hour and 98% by the sixth hour, and thus the formulation is unable to provide 24 hour therapeutic coverage.

EP 0393572 A2, EP 0250374 B1 and U.S. Pat. Nos. 9,642,809 and 5,165,937, all of which have been incorporated by reference herein, have made attempts at controlled release of flavoxate. For instance, U.S. Pat. No. 9,642,809 describes controlled release of the drug by incorporating it in a water-soluble micro-crystalline matrix. EP 0250374 attempts to control release by incorporating the drug into a swellable deposit core with a barrier and surrounded by mini-units containing fraction of the therapeutic dose. Aqueous fluids cause the core to swell and apply pressure on the core and mini units to dispense the drug. EP 0250374 B1 teaches that, of the 36 mg of flavoxate in uncoated and coated 60 mg mini units, 76% and 89% release take place in 3 and 6 hours respectively in vitro. Further, as a 60 mg of mini unit holds only 36 mg of flavoxate, EP 0250374 B1 teaches a drug-excipient ratio of 60:40 that is unsuitable for single dose delivery of 600 mg or 800 mg flavoxate. EP 0393572 A2 and U.S. Pat. No. 5,165,937 teach that "[f] lavoxate hydrochloride is in itself hardly compressible" and describes the preferred use of PVA as a binder, which "makes large-scale use of excipients superfluous, thus enabling the tablet dimensions to be limited." These documents describe controlled release tablets having flavoxate within a matrix made of hydroxypropylmethylcellulose (HPMC) K15, polyvinyl alcohol (PVA) as binder, and an acidifying agent so as to stabilize the flavoxate from the basic environment of the gut. In terms of in vitro dissolution, data available on a tablet having 600 mg flavoxate shows about 50% release in 8 hours. The finished weight of a 600 mg and 800 mg flavoxate tablet was 780.2 mg and 1040.3 mg respectively (U.S. Pat. No. 5,165,937).

EP 0393572 A2 and U.S. Pat. No. 5,165,937 teach incorporation of acidifying agents among other additives and excipients in the oral dosage form for controlled release tablets of flavoxate salt. Addition of all the additives and excipients as indicated in the documents makes the tablets very bulky and reduces any room for increasing drug-loading of the flavoxate or salt thereof. Furthermore, such large tablets lead to patient's discomfort during oral route of administration thereby reducing patient compliance for the tablets of drug.

If it were possible to incorporate high dosages of lipophilic drugs such as 600 mg or 800 mg of flavoxate into a final sub-gram formulation, a single-tablet-a-day dosage regimen becomes possible. It would also be possible to use the same approach to reduce the size of other sub-800 mg tablets currently available in the market for more compliance-friendly versions in case of similar drugs.

Thus, clearly, there is an unmet need for a delivery system and dosage form that has a reduced size, favourable drug-excipient ratio, and has a relatively uniform and controlled release profile of lipophilic acid soluble drugs over a longer duration. The invention overcomes the challenges of administering lipophilic acid soluble drugs with relatively poor compressibility, such as flavoxate, in a single dose orally ingestible form to ensure a 24-hour minimum effective dose of at least 1 µg/ml in plasma by bringing down the ratio of excipients to the active ingredient, thus enabling higher drug loading in tablets.

SUMMARY OF THE INVENTION

The present invention relates to a controlled release oral formulation of a lipophilic acid soluble drug. The invention also relates to a solid controlled release drug delivery system with greater drug-loading efficiency. The formulations described herein have a favourable active drug-excipient ratio is provided such that the formulations have higher drug-loading without compromising physical and pharmaceutical parameters of the formulations. This surprisingly makes it possible, to deliver therapeutic levels of drug for up to 24 hours in a recipient through a single dose administration. The invention enables delivery of lipophilic acid soluble drugs such as flavoxate being dispensed throughout the gastro-intestinal tract. The present invention also discloses combinations of polymers, binders, and excipients that enable compressing flavoxate and dimensioning it to easily ingestible oral tablets that can carry a higher load of active ingredient compared to the excipients. Other aspects of the invention include methods of treating diseases or disorders responsive to flavoxate, such as, e.g., disorders of the genitourinary tract, including but not limited to pollakiuria; nocturia; dysuria; urgency; vesicle suprapubic pain; frequency; urinary incontinence originating from various pathological conditions, such as prostatitis, urethritis, cystitis, urethero-cystitis, uretherotrigonitis, and the side effects of radiotherapy or surgical therapy of the urinary tract; vesico-urethral spasm due to catheterization, cystoscopy, or indwelling catheter; irritative symptoms of benign prostatic hyperplasia (BPH) and overactive bladder; or as a preventative prior to cystoscopy, catheterization, or sequelae of surgical intervention of the lower urinary tract.

In an embodiment the present invention provides a controlled release oral formulation comprising about 400 to 800 mg of flavoxate salt as an active ingredient, suitable polymers, binders and excipients; and wherein the oral formulation is free of acidifying agent and the salt may be flavoxate hydrochloride.

In still another embodiment in the controlled release oral formulation the suitable polymers are selected from the group comprising of methylcelluloses, polyvinyl alcohols, acrylic copolymers, ethylcellulose, hydroxypropylmethylcellulose (HPMC), HPMC K4M, HPMC K15M, HPMC K100M or combination thereof.

In yet another embodiment in the controlled release oral formulation the ratio of said suitable polymers and/or excepients to flavoxate salt is about 8:1 to 100:1.

In another embodiment in the controlled release oral formulation the binder is polyvinylpyrrolidone (PVP K 30).

In yet another embodiment in the controlled release oral formulation the ratio of said binders and flavoxate salt about 1:2.

In still another embodiment in the controlled release oral formulation the binder is dispersed in water, ethanol, acetonitrile, acetone, IPA (Isopropyl alcohol) or mixture thereof.

In another embodiment in the controlled release oral formulation the excipients are selected from the group comprising of magnesium stearate, talc, colloidal silica, isopropyl alcohol, lactose, microcrystalline cellulose or combination thereof.

In yet another embodiment in the controlled release oral formulation the formulation is in a solid dosage form preferably as a tablet.

In still another embodiment in the tablet has a thickness of about 6.20 mm to about 6.90 mm.

In yet another embodiment the tablet has a thickness of preferably about 5.27 mm to about 6.20 mm.

In another embodiment in the controlled release oral formulation the tablet has a hardness of about 6 kg/cm$^2$ to about 20 kg/cm$^2$.

In yet another embodiment in the controlled release oral formulation the tablet has micronized granules of drug of particle size with D90 of about 10 to 100 µm. In still another embodiment in the controlled release oral formulation the tablet has micronized granules of drug of particle size preferably with D50 of less than about 15 µm.

In yet another embodiment in the controlled release oral formulation xhibits pH independent release profile.

In another embodiment the controlled release oral formulation releases flavoxate hydrochloride throughout a course of 12-24 hours.

In yet another embodiment the controlled release oral formulation is free from risk of alcohol dose dumping.

In still another embodiment the controlled release oral formulation is a solid dosage form comprising a core containing an active ingredient, suitable polymers, binders and excipients; and a polymeric coating on surface of the core.

In yet another embodiment in the controlled release oral formulation the polymeric coating comprises a polymer dissolved in excipients.

In still another embodiment in the controlled release oral formulation the excipients in the coating are selected from group comprising of isopropyl alcohol, ethanol, acetonitrile, chloroform, methylene chloride, acetone or mixture thereof.

In yet another embodiment in the controlled release oral formulation the coating further comprises PEG (Polyethylene glycol).

In another embodiment the controlled release oral formulation releases at least 10-15% of the flavoxate salt within 1 hour, achieves plasma concentrations greater than or equal to 1 mcg/ml and the rest of the drug releases flavoxate salt over 24 hours, achieves plasma concentrations of 1 mcg/ml for 24 hours.

In yet another embodiment the controlled release oral formulation achieves greater than or equal to 1 mcg/ml plasma concentrations of the metabolite of Flavoxate i.e. 3-methylflavone-8-carboxylic acid (MFCA) at about 1 hour and no later than two and a half hours, most preferably at about two hours.

In still another embodiment present invention provides a method of treating at least one symptom of pollakiuria, nocturia, dysuria, urgency, vesicle suprapubic pain, frequency, urinary incontinence originating from various pathological situations such as prostatitis, urethritis, cystitis, urethero-cystitis, uretherotrigonitis, relief of vesico-urethral spasms due to catheterisation, cystoscopy or indwelling catheters; prior to cystoscopy or catheterisation; sequelae of surgical intervention of the lower urinary tract and/or the side effects of radiotherapy or surgical therapy of the urinary tract which comprises administering a formulation as described hereinabove.

In another embodiment the controlled release oral formulation elicits a minimum effective concentration in the patient's plasma of at least about 1 µg/mL flavoxate salt for at least 24 hours.

In yet another embodiment the present invention provides a controlled release oral formulation for treatment or symptomatic relief of pollakiuria, nocturia, dysuria, urgency, vesicle suprapubic pain, frequency, urinary incontinence originating from various pathological situations such as prostatitis, urethritis, cystitis, urethero-cystitis, uretherotrigonitis, relief of vesico-urethral spasms due to catheterisation, cystoscopy or indwelling catheters; prior to cystoscopy or catheterisation; sequelae of surgical intervention of the lower urinary tract and/or the side effects of radiotherapy or surgical therapy of the urinary tract.

In another embodiment the present invention provides a method of preparing controlled release oral formulation of about 400 to 800 mg of flavoxate salt as an active ingredient comprising steps of:
(a) mixing flavoxate salt with one or more polymers to obtain a mixture;
(b) moistening the mixture obtained in step (a) with dispersed PVPK30 to obtain a wet mass;
(c) granulating the wet mass obtained in step (b) by passing through suitable screen to obtain granules;
(d) drying the granules obtained in step (c); and
(e) lubricating the dried granules of step (d) with suitable lubricants followed by compressing.

In yet another embodiment in the method provided hereinabove lubrication of dried granules in step (e) is further followed by micronization by milling.

In still another embodiment in the method provided hereinabove micronization is carried to obtain a particle size with D90 of about 10 to 100 µm.

In another embodiment in the method provided hereinabove compressed tablets obtained are further treated with polymeric coating.

In yet another embodiment in the method provided hereinabove in step (b) the dispersed PVPK30 is obtained by dispersion in one or more of water, ethanol, acetonitrile, acetone, IPA.

In another embodiment in the method provided hereinabove in step (e) the suitable lubricants are selected from the group consisting of talc, magnesium stearate, stearic acid, colloidal silica or mixture thereof.

In an embodiment the present invention provides a formulation comprising about 400 mg to about 800 mg flavoxate salt as an active ingredient and further comprising hydroxypropylmethylcellulose (HPMC) K4M and HPMC K15M, wherein the formulation does not comprise an acidifying agent.

In another embodiment the present invention provides that the formulation comprises about 82% (w/w %) flavoxate salt.

In still another embodiment the present invention provides that the flavoxate salt is flavoxate hydrochloride.

In yet another embodiment the formulation further comprises HPMC K100M.

In a further embodiment the formulation described hereinabove comprises polyvinylpyrrolidone (PVP) K30.

In an additional embodiment the formulation described hereinabove comprises colloidal silicon dioxide.

In another embodiment the formulation further comprises lactose, microcrystalline cellulose, starch, and magnesium stearate, and optionally further comprises talc and/or isopropyl alcohol.

In still another embodiment the formulation comprises about 0.5% to about 5% HPMC K4M, about 8% to about 15% HPMC K15M, about 0.5% to about 2% HPMC K100M, about 4% to about 6% PVP K30M, about 0.8% to about 1% magnesium stearate, up to about 1% colloidal silicon dioxide, and up to about 5% lactose, and optionally further comprises about 1% to about 3% talc.

In yet another embodiment the formulation comprises about 0.5% to about 5% HPMC K4M, about 4% to about 15% HPMC K15M, about 0.5% to about 2% HPMC K100M, about 4% to about 6% PVP K30, about 0.5 to about 5% lactose, about 0.8% to about 1% magnesium stearate, and up to about 1% colloidal silicon dioxide, and optionally further comprises about 1% to about 3% talc.

In a further embodiment the formulation comprises about 400 mg, about 600 mg, or about 800 mg flavoxate hydrochloride.

In still further embodiment the formulation described hereinabove is formulated for oral delivery.

In another the formulation described hereinabove is formulated as a solid.

In still another embodiment the formulation described hereinabove is formulated as a tablet.

In yet another embodiment the formulation described hereinabove comprises a film coating.

In a further embodiment the formulation comprises about 800 mg flavoxate hydrochloride, about 19.5 mg HPMC K4M, about 58.5 mg HPMC K15M, about 8 mg HPMC K100M, about 48.5 mg PVP K30, about 10 mg magnesium stearate, about 25 mg lactose, and about 4 mg colloidal silicon dioxide.

In an additional embodiment the formulation comprises about 800 mg flavoxate hydrochloride, about 100 mg HPMC K15M, about 8 mg HPMC K100M, about 50 mg PVP K30, about 10 mg magnesium stearate, and about 4 mg colloidal silicon dioxide.

In still another embodiment the formulation comprises about 600 mg flavoxate hydrochloride, about 14.6 mg HPMC K4M, about 44 mg HPMC K15M, about 6 mg HPMC K100M, about 36.5 mg PVP K30, about 7.5 mg magnesium stearate, about 19 mg lactose, and about 3 mg colloidal silicon dioxide.

In yet another embodiment the formulation comprises about 600 mg flavoxate hydrochloride, about 75 mg HPMC K15M, about 6 mg HPMC K100M, about 37.5 mg PVP K30, about 7.5 mg magnesium stearate, and about 3 mg colloidal silicon dioxide. In a further embodiment the formulation releases flavoxate salt throughout a course of up to 24 hours.

In an additional embodiment the formulation releases flavoxate salt with a 12 hour to 24 hour release profile.

In an embodiment the formulation comprises about 400 mg to about 800 mg flavoxate salt as an active ingredient and further comprising hydroxypropylmethylcellulose (HPMC) K4M and HPMC K15M, wherein the formulation does not comprise an acidifying agent, wherein the formulation exhibits the dissolution profile of (a) 5-30% in 1 hour; (b) 45-85% in 8 hours and (c) not less than 85% in 24 hrs.

In yet another embodiment the formulation exhibits a pH-independent release profile.

In still another embodiment the formulation releases at least 10-15% of the flavoxate salt within 1 hr, achieves plasma concentrations greater than or equal to 1 mcg/ml and the rest of the drug releases flavoxate salt over 24 hours, achieves plasma concentrations of 1 mcg/ml for 24 hours.

In an embodiment the present invention provides a method of making a tablet comprising flavoxate hydrochloride, the method comprising: (a) combining flavoxate hydrochloride with HPMC K4M, HPMC K15M, and HPMC K100M to form a mixture; (b) moistening the mixture of (a) with PVP K30, with or without lactose, in isopropyl alcohol to form a wet mass; (c) granulating the wet mass of (b) to form granules; (d) drying the granules of (c) to form dry granules; (e) lubricating the dry granules of (d) with magnesium stearate and colloidal silicon dioxide to form a formulation; and (f) compressing the formulation of (e) to form the tablet.

In a further embodiment the method further comprises coating the tablet.

In still another embodiment the present invention provides the method of treating at least one symptom of pollakiuria, vesico-urethral spasm, prostatic hyperplasia, or overactive bladder in a patient.

In yet another embodiment of the present invention the formulation elicits a minimum effective concentration in the patient's plasma of at least about 1 μg/mL flavoxate salt for at least 24 hours.

In a further another embodiment the present invention provides use of the formulation described hereinabove for treatment or symptomatic relief of pollakiuria, nocturia, dysuria, urgency, vesicle suprapubic pain, frequency, urinary incontinence originating from various pathological situations such as prostatitis, urethritis, cystitis, urethero-cystitis, uretherotrigonitis, relief of vesico-urethral spasms due to catheterisation, cystoscopy or indwelling catheters; prior to cystoscopy or catheterisation; sequelae of surgical intervention of the lower urinary tract and/or the side effects of radiotherapy or surgical therapy of the urinary tract.

BRIEF DESCRIPTION OF THE DRAWINGS

FIGS. 2A and 2B depict comparisons of flavoxate hydrochloride (600 mg and 800 mg) controlled-release tablets of the invention and flavoxate hydrochloride tablets of U.S. Pat. No. 5,165,937 (600 mg and 800 mg).

DETAILED DESCRIPTION OF THE INVENTION

Definitions

Figure 1A:
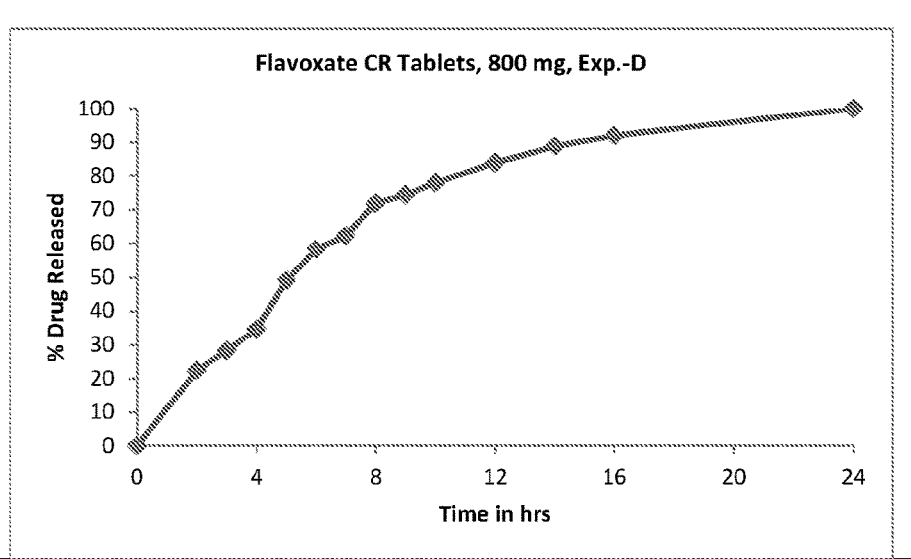
FIGS. 1A, 1B, 1C, 1D, 1E, 1F, and 1G show in vitro drug-release graphs. The percentage of drug released over time is depicted for the film-coated 800 mg and 600 mg flavoxate controlled release formulations.

All numbers herein may be understood as modified by "about," which, when referring to a measurable value such as an amount, a temporal duration, and the like, is meant to encompass variations of ±5%, preferably ±2%, more preferably ±1%, and further preferably ±0.5% from the specified value, as such variations are appropriate to obtain a desired amount of drug, unless otherwise specified.

The terms "composition" and "formulation" are used interchangeably herein to refer to a flavoxate hydrochloride containing drug product in a solid oral dosage form.

The terms "flavoxate" and "flavoxate hydrochloride" are used interchangeably to refer to the active ingredient in the compositions of the invention, 2-piperidinoethyl-3-methyl-flavone 8-carboxylate hydrochloride.

Flavoxate has been used therapeutically for symptomatic relief of pollakiuria, particularly nocturia, dysuria, urgency, vesicle suprapubic pain, frequency and urinary incontinence originating from various pathological situations such as prostatitis, urethritis, cystitis, urethra-cystitis, uretherotrigonitis and the side effects of radiotherapy or surgical therapy of the urinary tract. In addition flavoxate is indicated for the relief of vesico-urethral spasm due to catheterization, cystoscopy or indwelling catheter, prior to cystoscopy or catheterization, sequelae of surgical intervention of lower urinary tract. It is also used for the irritative symptoms of benign prostatic hyperplasia (BPH) and overactive bladder. It inhibits the phosphodiesterase enzyme and, by calcium antagonistic action, relaxes smooth muscle. The drug preferentially acts on the genito-urinary tract and not the intestine. Because the drug has a short half-life, maintaining effective therapeutic levels (at least 1 μg/ml) of the drug in circulation over a 24-hour period remains a challenge. Because an existing regimen of administering 100 or 200 mg of flavoxate requires consumption of many tablets during the day, patient-compliance becomes difficult and often lapses. The pharmacokinetic challenges as so substantial that, despite the passage of 50 years, the therapeutic dosage regimen has not significantly varied. There is, therefore, a need in the art to incorporate a higher dose into a single tablet that can be orally administered and will provide a 24-hour therapeutic effect.

The release profile of controlled-release formulations depends on a variety of factors, such as properties of the pharmaceutical dosage form per se, nature and content of the matrix, nature of the release medium, nature and content of the active compound, nature and content of further pharmaceutical excipients as well as the interrelationship of these factors. It is well known that depending on how a pharmaceutically active ingredient is formulated into a tablet, its release pattern can be modified. In this regard, tablets providing a delayed or controlled release profile are of primary importance. With delayed or controlled release tablets, care has to be taken that under no circumstances the pharmaceutically active ingredient will be released completely and instantaneously in an uncontrolled manner, since regularly the dosage used for delayed or controlled release tablets is much higher than for non-delayed or controlled release tablets. Otherwise, such "dose-dumping" may cause serious adverse effects.

Previous studies had shown that the 200 mg dosage regimen was near ineffective and the 400 mg/600 mg dosage can be therapeutically effective. The Japanese clinical study, (Nijima et al.: A multicenter clinical trial of flavoxate hydrochloride. Nishinippon Hinyokika 1981; 43: 1055-1063) concluded that an effective way to improve the therapeutic activity of flavoxate hydrochloride is to increase its dose to 1200 mg/day.

Hence, another challenge is to keep the excipient amounts low so that the final form of the drug formulation will have a practically and commercially acceptable size. Flavoxate is poorly compressible and therefore, poses another challenge for molding into compact orally-administered tablets. Hard tablets are desirable also because they do not overly disintegrate, which would result in dose-dumping or immediate release of large quantity of active drug. Thus sustained release of low amounts of the drug over a 24 hour period would be an ideal dosing regimen.

While preparing tablets of flavoxate salt, dry granules comprising flavoxate hydrochloride can be subjected to particle size reduction prior to compressing for tablet formation. This is generally done to increase the specific surface of the active ingredient and bioavailability of a poorly soluble drug. This can be achieved by micronization technique, which is known in the art, and provides a final particle size of less than 100 μm.

As stated earlier, incorporation of acidifying agents among other additives and excipients in the oral dosage form for controlled release tablets of flavoxate salt makes the tablets very bulky and reduces any room for increasing drug-loading of the flavoxate or salt thereof. Furthermore, such large tablets lead to patient's discomfort during oral route of administration thereby reducing patient compliance for the tablets of drug. But the challenge for the formulation (s) of flavoxate sans acidifying agents is that flavoxate is not very soluble in its unsalified form and it has been found that an acidifying agent is needed to incorporate flavoxate in appropriate quantities and to facilitate controlled release of flavoxate.

The present inventors have, after extensive research and experimentation, succeeded in increasing the drug-loading capacity of the solid controlled release formulation. The inventors have surprisingly formulated a sub-gram tablet that incorporates 600 mg or 800 mg of flavoxate and releases it slowly over at least 24 hours in the bloodstream, to maintain 1 μg/ml drug concentration in plasma. These formulations further achieve pH-independent controlled release. The inventors have surprisingly achieved this formulation and its pH-independent controlled release without employing acidifying agent(s) in the formulation.

The inventors of present invention found better performance of drug formulations with PVP K-30 (which is more hydrophilic than PVA & Cellulose) as binder in combination with other formulation ingredients viz. Polymers, Colloidal Silicon dioxide. The inventors also employed hydrophilic matrix polymers HPMC K4M, HPMC K15M and HPMC K100M achieve the desired release profile. Water soluble binder, PVP K-30, is employed for formulating the granules. Without being bound by theory, it is believe that these hydrophilic matrices control the drug release in at least two ways: HPMC K100M swells and makes intact matrices around the drug; at the same time, HPMC K4M and/or HPMC K15M provide a barrier of low viscosity and therefore, channel the drug out slowly from the intact matrix, allowing the drug release over a controlled period of time.

With the use of a unique combination of polymers, water soluble binder, and excipient(s) like 'Colloidal Silicon dioxide' the inventors have significantly and unexpectedly improved compressibility characteristics of flavoxate while maintaining tablet weight at sub-gram levels and tablet dimensions that are easily ingestible even at the high dose strength of 800 mg.

Although prior art suggests that an acidifying agent must be required to ensure the solubility of Flavoxate, the use of these polymers in combination as mentioned in the present invention and further use of water soluble binder (PVP K 30) a suitable CR dosage form that releases over a period of 24 hours duration along with better compressibility of the drug is achieved. The CR formulation of present invention is prepared without employing acidifying agent and unexpectedly results in pH independent release profile of the finished formulation.

A sub-gram tablet has been surprisingly formulated in the present invention that can incorporate 600/800 mg of slow-releasing flavoxate and release it over 24 hours in the blood-stream maintaining 1 μg/ml drug concentration. It had hitherto been impossible to incorporate such large dosage within a single conventional-sized orally ingestible tablet. The experiments have resulted in a surprising finding that excipient to active principle ratio can be kept low so that contrary to conventional pharmaceutics, where the excipient makes up 40-50% of the tablet composition, the instant invention manages to keep the excipient proportion at 20-25% of the overall tablet weight, thus enabling higher drug loading within a smaller tablet size. This would enable not only size-reduction for 800 mg dose tablets, but also for lower dosage versions that could benefit from addition of other combination drugs too without concomitant loss of characteristics of the formulation. Also, the invention provides a mechanism to incorporate and deliver lipophilic drugs with poor aqueous solubility by the methods disclosed herein.

The invention will be better illustrated with examples of flavoxate formulations incorporating dosages of 400, 600 and 800 mg in an easily-ingestible single tablet.

Preparation of Flavoxate Formulations

A multi-step process was adopted to develop the drug formulation:
1. Selection of polymers, binders and excipients.
   a) Initial batches were prepared with various binders for optimization.
   b) Selection of drug retardant polymers:
      For stomach and colon: Low density and low-viscosity polymers like hydroxypropyl methylcellulose (HPMC) HPMC K15M, HPMC K4M were selected and combined with HPMC K100M
      Effect of Eudragit and ethyl cellulose was also investigated
2. Optimization of the combinations of polymers, binders and excipients and their respective ratios with drug to obtain granules of formulation; tablet-weight; hardness and release profile.

3. Optional micronization of granules by milling of formulation prepared.
4. Compression of the composition into a tablet of acceptable weight and size.
5 Coating of the tablets formed.

The polymers and excipient used were selected based on materials and their known properties and combined into a composition so as to incorporate 400, 600 and 800 mg of drug into a single tablet with a hardness in the range of about 8 to 20 Kg/cm$^2$ and with thickness between about 6.20 to about 6.90 mm (800 mg) or between about 5.27 to about 6.20 mm (600 mg).

Figure 8:
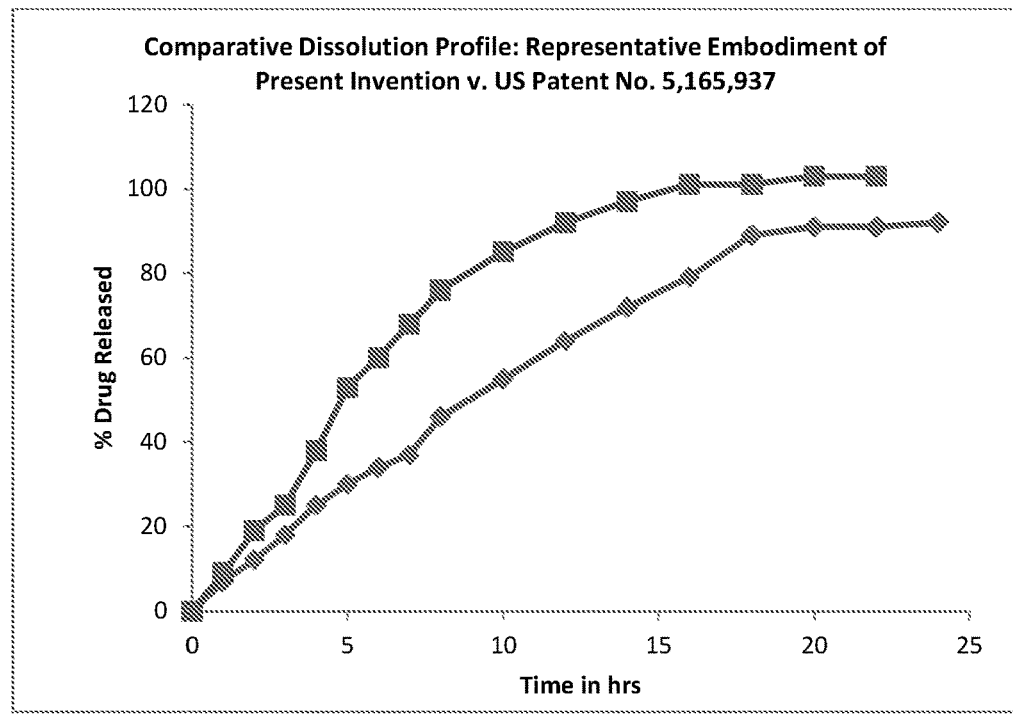
FIG. 8 depicts the comparative drug release profile of a formulation as described in U.S. Pat. No. 5,165,937 and a representative formulation of the invention.

The inventors of the present invention have made a unique use of HPMC K4M and/or or HPMC K15, alone or in combination with HPMC K100M and optionally PVP K30, to impart desirable drug release profile to the formulations. It was not possible to predict the resulting properties of particular combinations of excipients to determine whether any combination could provide a formulation that would be stable and robust. Even though many of the constituents of the formulation are already known in the art, in more than 50 years of need, there are no verified reports of a controlled release formulation in single-tablet form that sustains protective levels of the drug in plasma for 24 hours. In the inventors' hands, the controlled release formulation described in U.S. Pat. No. 5,165,937 is fully released by 16 hours (FIG. 8). The inventors' combinations and permutations of excipients have surprisingly enabled the development of a single-tablet formulation that releases the drug at therapeutic concentrations through a 24 hr duration (FIG. 8).

Figure 2B:
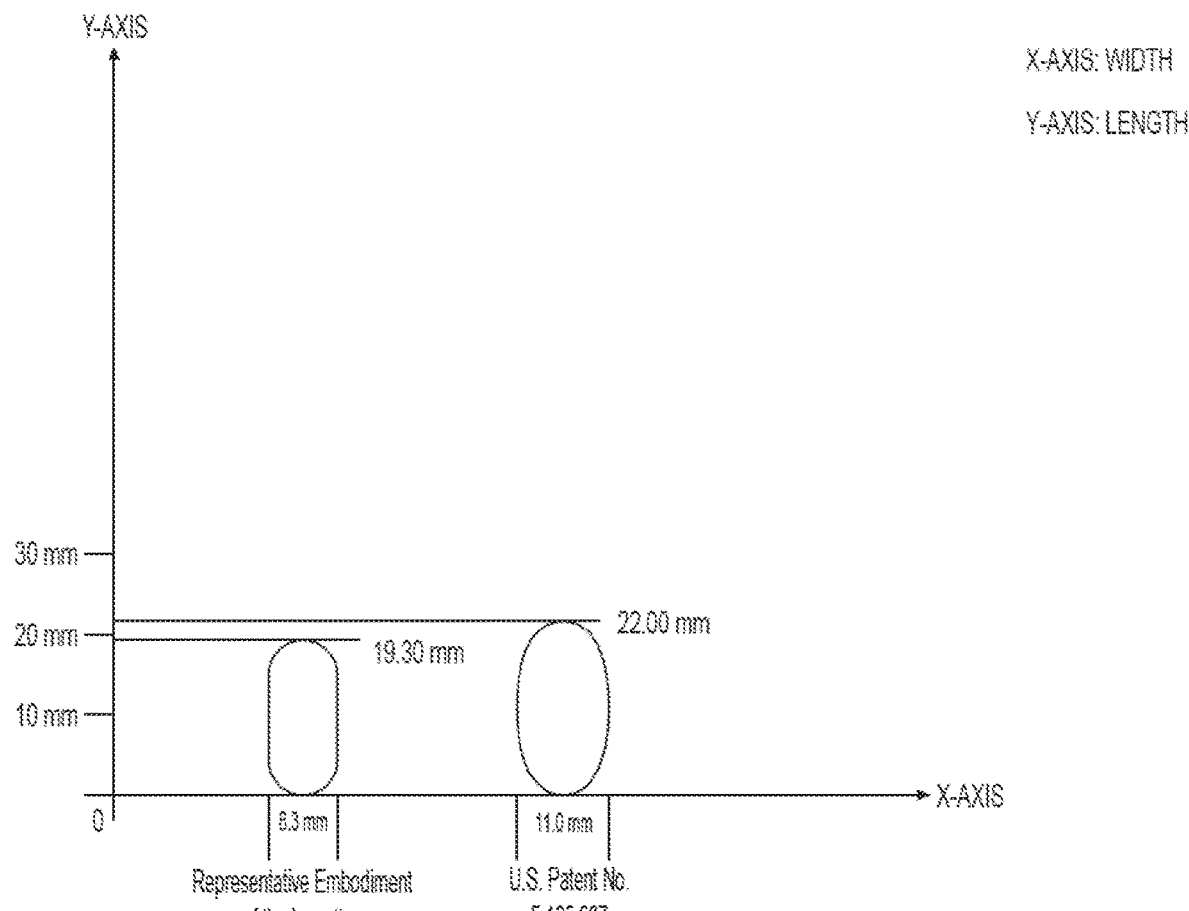

FIGS. 2A and 2B show pictures compare the dimensions of flavoxate hydrochloride (600 mg and 800 mg) controlled release tablets of the present invention and of flavoxate hydrochloride tablets of U.S. Pat. No. 5,165,937 (600 mg and 800 mg). It is clear that the tablets prepared according to the present invention have a substantially reduced size relative to the tablets taught by U.S. Pat. No. 5,165,937. This result is surprising given the poor compressibility of flavoxate, and demonstrates a substantial improvement for patients who struggle or refuse to ingest large tablets.

In some embodiments, the invention relates to a formulation comprising flavoxate salt (e.g., flavoxate hydrochloride) and one or more excipients, wherein the formulation comprises about 400 mg to about 800 mg flavoxate salt as an active ingredient and wherein the formulation does not comprises an acidifying agent. In some aspects, the one or more excipients comprise hydroxypropylmethylcellulose HPMC K4M and HPMC K15M, and optionally HPMC K100M. In some aspects, the formulation further comprises polyvinylpyrrolidone (PVP) K30, magnesium stearate, and colloidal silicon dioxide, and, optionally, lactose, microcrystalline cellulose, starch, talc, and/or isopropyl alcohol.

In some embodiments, the invention relates to a formulation comprising flavoxate salt (e.g., flavoxate hydrochloride) and one or more excipients, wherein about 77 to 82% (w/w %) of the total weight of the composition consists of flavoxate salt (e.g., flavoxate hydrochloride). In some aspects of these embodiments, the one or more excipients comprise hydroxypropylmethylcellulose (HPMC); HPMC K4M HPMC K15M, HPMC K100M, polyvinylpyrrolidone (PVP) K30, magnesium stearate, and colloidal silicon dioxide, and optionally talc and/or isopropyl alcohol.

In some embodiments, the invention relates to a formulation comprising flavoxate salt (e.g., flavoxate hydrochloride) and one or more excipients, wherein about 82% of the total weight of the composition consists of flavoxate salt (e.g., flavoxate hydrochloride). In some aspects of these embodiments, the one or more excipients comprise different grades of hydroxypropylmethylcellulose HPMC viz. HPMC K4M, HPMC K15M, HPMC K100M, polyvinylpyrrolidone (PVP) K30, magnesium stearate, and colloidal silicon dioxide, and, optionally, lactose, microcrystalline cellulose, starch, talc, and/or isopropyl alcohol.

In some embodiments, the invention relates to a formulation comprising flavoxate hydrochloride and one or more excipients, wherein the one or more excipients comprise one or more HPMC molecules, wherein the w/w ratio of flavoxate hydrochloride to the one or more HPMC molecules may range from 8:1 to 100:1. In some aspects of these embodiments, the one or more HPMC molecules comprise HPMC K4M, HPMC K15M, and HPMC K100M. In some aspects of these embodiments, the one or more HPMC molecules comprise HPMC K4M, HPMC K15M, and HPMC K100M and the one or more excipients further comprise PVP K30, magnesium stearate, and colloidal silicon dioxide, and, optionally, lactose, microcrystalline cellulose, starch, talc and/or isopropyl alcohol.

In some aspects of the above embodiments, the formulation comprises about 0.5% to about 5% HPMC K4M, about 8% to about 15% HPMC K15M, about 0.5% to about 2% HPMC K100M, about 4% to about 6% PVP K30M, about 0.8% to about 1% magnesium stearate, and up to about 1% colloidal silicon dioxide, and optionally about 5% of lactose, about 4% of Microcrystalline Cellulose, about 4% of Starch, and about 1% to about 3% talc.

In some aspects of the above embodiments, the formulation comprises up to about 800 mg flavoxate hydrochloride. For example, the formulation may comprise about 400 mg, about 600 mg, or about 800 mg flavoxate hydrochloride.

In some aspects of the above embodiments, the formulation is an oral formulation, for example a solid oral formulation. In some aspects, the formulation is a tablet.

In some aspects, the formulation is a single-dose tablet. In some aspects, the formulation further comprises a film coating.

In some aspects of the above embodiments, the formulation has thickness of about 6.20 mm to about 6.90 mm.

In some aspects of the above embodiments, the formulation has thickness preferably of about 5.27 mm to about 6.20 mm.

In some aspects of the above embodiments, the formulation has hardness of about 6 kg/cm$^2$ to about 20 kg/cm$^2$.

In some aspects of the above embodiments, the formulation has hardness of about 8 kg/cm$^2$ to about 10 kg/cm$^2$.

In some aspects, the tablet has a width of about 7.5 mm and a length of about 17.5 mm. In some aspects, the tablet has a width of about 8.3 mm and a length of about 19.3 mm.

In some embodiments of the invention, the formulation comprises about 800 mg flavoxate hydrochloride, about 4 mg HPMC K4M to about 50 mg HPMC K4M, about 100 mg HPMC K15M, about 8 mg HPMC K100M, about 50 mg PVP K30, about 10 mg magnesium stearate, and about 4 mg colloidal silicon dioxide. In some embodiments, the formulation comprises about 800 mg flavoxate hydrochloride, about 19.5 mg HPMC K4M, about 58.5 mg HPMC K15M, about 8 mg HPMC K100M, about 48.5 mg PVP K30, about 10 mg magnesium stearate, about 25 mg lactose, and about 4 mg colloidal silicon dioxide.

In some embodiments of the invention, the formulation comprises about 600 mg flavoxate hydrochloride, about 4 mg HPMC K4M to about 50 mg HPMC K4M, about 75 mg HPMC K15M, about 6 mg HPMC K100M, about 37.5 mg PVP K30, about 7.5 mg magnesium stearate, and about 3 mg colloidal silicon dioxide. In some embodiments, the formulation comprises about 600 mg flavoxate hydrochloride, about 14.5 mg HPMC K4M, about 44 mg HPMC K15M, about 6 mg HPMC K100M, about 36.5 mg PVP K30, about 7.5 mg magnesium, about 19 mg lactose, and about 3 mg colloidal silicon dioxide.

In some aspects, the formulation is a round bi-convex tablet. In some aspects, the formulation is an oval, elongated tablet.

In some aspects, the tablet has a width of about 7.5 mm and a length of about 17.5 mm.

In some aspects of any of the above embodiments, the formulation releases flavoxate hydrochloride throughout a course of at least 12 hours. In some aspects of any of the above embodiments, the formulation releases flavoxate hydrochloride throughout a course of at least 14 hours. In some aspects of any of the above embodiments, the formulation releases flavoxate hydrochloride throughout a course of at least 16 hours. In some aspects of any of the above embodiments, the formulation releases flavoxate hydrochloride throughout a course of at least 24 hours. In some aspects of any of the above embodiments, the formulation releases flavoxate hydrochloride throughout a course of about 12 to about 24 hours.

In some embodiments, the invention relates to a method of making a tablet comprising flavoxate hydrochloride, the method comprising (a) combining flavoxate hydrochloride with HPMC K4M, HPMC K15M and HPMC K100M to form a mixture; (b) moistening the mixture of (a) with PVP K30 in isopropyl alcohol to form a wet mass; (c) granulating the wet mass of (b) to form granules; (d) drying the granules of (c) to form dry granules; (e) lubricating the dry granules of (d) with magnesium stearate and colloidal silicon dioxide to form a formulation; and (f) compressing the formulation of (e) to form the tablet.

In some aspects, the method or making a tablet further comprises coating the tablet.

In some embodiments, the invention relates to the use of any of the formulations described herein as a controlled-release treatment in a patient in need thereof. For example, the formulations described herein may be used in a controlled-release treatment of at least one symptom of pollakiuria, vesico-urethral spasm, prostatic hyperplasia, or overactive bladder. In some aspects, the formulation elicits a minimum effective concentration in the patient's plasma of at least about 1 μg/mL flavoxate hydrochloride for at least 24 hours.

The invention is further illustrated with examples below, which should in no way be construed as limiting the invention.

Characterization of Drug Molecule

The melting point of flavoxate hydrochloride is 235.2 degree Celsius, as measured with a melting point apparatus by capillary method. Fourier-transform infrared (FTIR) Interpretation of Flavoxate Hydrochloride (Pure Drug) is shown in FIG. 3.

Interpretation

Drug identification was performed using the FTIR spectrum of pure drug i.e. flavoxate hydrochloride having molecular formula of $C_{24}H_{25}NO_4 \cdot HCl$.

Figure 3:
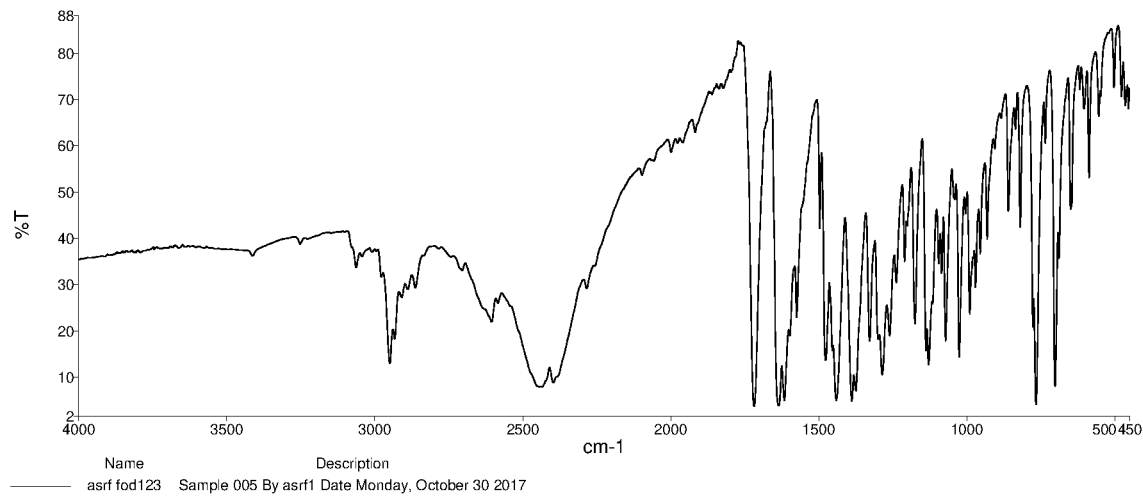
FIG. 3 shows the FTIR Interpretation of Flavoxate Hydrochloride (pure drug).

The following characteristic peaks were observed for pure flavoxate in fingerprint region as shown in FIG. 3.

1. 3415 $cm^{-1}$ due to tertiary amine
2. 2944 $cm^{-1}$ due to C—H stretching in CH3 (alkanes)
3. 1598 $cm^{-1}$ and 1400 $cm^{-1}$ due to C=C aromatic stretching (Phenyl ring)
4. 1700 $cm^{-1}$ due to C=O carbonyl peak FTIR results observed from FIG. 3 exhibited no change in prominent peaks of drug molecule as compared with reference.

Pre-Formulation Study:

The following physico-chemical characteristics of the drug substance were studied for their effect on drug product development, manufacture and performance.

Solubility

Flow properties:
1. Tapped density
2. Bulk density
3. Compressibility Index and Hausner ratio
4. Angle of repose Solubility:

Solubility of flavoxate hydrochloride was determined in various aqueous buffers, water, ethanol, acetone and ethyl ether at 20° C. and at ambient temperature (20 to 25° C.).

TABLE 1

Solubility of flavoxate in various solvents at 20° C.

| Media | % w/v |
|---|---|
| Water | 0.75 |
| Methanol | 0.90 |
| Ethanol | 0.20 |
| Acetone | Insoluble |
| Ethyl Ether | Insoluble |
| Chloroform | 2.50 |

TABLE 2 pH-dependent aqueous solubility of flavoxate at ambient temperature (20 to 25° C.)

| Media | pH | Solubility mg/ml |
|---|---|---|
| Water | 5.7 | 11.30 |
| 0.1N HCl | 1.2 | 0.57 |
| 0.05N Phosphate Buffer | 2.5 | 7.64 |
| 0.05N Phosphate Buffer | 4.5 | 13.68 |
| 0.05N Phosphate Buffer | 6.0 | 15.43 |
| 0.05N Phosphate Buffer | 6.8 | 6.17 |
| 0.05N Phosphate Buffer | 7.2 | 1.04 |
| 0.05N Phosphate Buffer | 7.5 | 0.58 |

Flow Properties:

Flowability measures how uniformly the powder flows from the hopper into the tablet die and is an index of how well the tablet die will be filled to a constant volume. Particles less than 10 μm were seen to have excessive cohesive forces and did not flow freely while particles with the size of greater than or equal to 250 μm flowed freely. Similarly, the angle between the freestanding surface of a powder heap and horizontal plane is the angle of repose. Powders that have lower angle of repose exhibit better flows. At 35° C. flowability was less and could be improved with addition of lubricants during tablet-making.

Results of tests to determine the Angle of repose (35°), Carr's index (33.3%), bulk density (0.236 gm/ml) and tapped density (0.355 mg/ml) indicate that the drug powder had poor flow properties. Hence a granular mixture having different excipients had to be prepared to improve the flow properties of drug. Flow properties of granular blend showed that powder blend have good flow properties in comparison to drug molecule powder.

The present invention is illustrated with examples below, which should in no way be construed as limiting the invention.

Example 1

Experiments were conducted to ascertain compatibility of the drug with commonly used excipients. Independently each excipient was mixed with the drug and the samples analyzed for physical change as well as related substances at accelerated and stressed condition of 1 Month at 40° C. and 75% relative humidity. The total released substance (RS) value of initial compatibility samples did not show any substantial change in comparison to control samples (Pure drug alone). Also the range for total RS value was comparable to the control even in stressed condition. Thus, the drug was found to be compatible with all the tested excipients, including all excipients selected for the final formulation.

TABLE 3

Total RS values of the drug-excipient compatibility

| Name of Excipient Excipient Name | Drug:Excipient Ratio | Total R.S. (%) Initial | 30 D/40° C./ 75% RH* |
|---|---|---|---|
| API | 1 | 0.02 | 0.04 |
| API + HPMC K 15 | 1:10 | 0.02 | 0.04 |
| API + HPMC K 100 | 1:10 | 0.02 | 0.05 |
| API + PVP K 30 | 2:1 | 0.02 | 0.05 |
| API + Mg stearate | 2:1 | 0.02 | 0.06 |
| API + Colloidal silicon dioxide | 2:1 | 0.02 | 0.07 |

Example 2

Process of Making Flavoxate Tablets:

Flavoxate hydrochloride is passed through a 100-mesh screen eliminate lumps. The drug was then mixed with ethyl cellulose, HPMC K4M, HPMC K15M, or HPMCK 100, or a combination thereof. The mixture was moistened with PVPK30 dispersion in purified water, ethanol, acetonitrile, acetone, IPA (Isopropyl alcohol), or a combination thereof, and the wet mass was granulated by passing through a suitable screen. The granules were then dried in a suitable drier. The dry granules were lubricated with talc, magnesium stearate, stearic acid, colloidal silica alone or in combination and subsequently compressed in a rotary tablet machine using concave punches.

Particle Size Reduction of Flavoxate Hydrochloride:

Product particles (dry granules) were fed into the milling chamber through an injector. High-velocity air is introduced into the mill through jet nozzles placed around the circular chamber of the mill. Particles are consequently accelerated inside the milling chamber and dragged in a spiral movement causing them to collide repeatedly. They break up into progressively small particles until the accumulated energy is reduced to negligible values and desired particle size of about D90 ranging from about 10 to about 100 μm. The micronization is preferably carried out such that the micronized granules of drug of particle size, preferably with D50 of less than about 15 μm, are obtained. Any exhaust air carrying micronized particles is fed into a suitable de-dusting unit.

Example 3

Coating the Tablet

TABLE 4

Excipients used in coating of tablets

| S.No | Excipients | Qty for 500 tablets size in g |
|---|---|---|
| 1 | Isopropyl alcohol, ethanol, acetonitrile, chloroform | 300-400 g |
| 2 | Methylene chloride, acetone | 600-900 g |
| 3 | Opadry white, Eudragit, Ethyl cellulose, Povidone | 20-60 g |
| 4 | Polyethylene glycol 200/400/4000/6000 | 5-15 g |

Process of Making the Coating Solution:

The polymer was dissolved in ethanol, acetonitrile or chloroform or isopropyl alcohol in a stainless-steel container with constant stirring and Methylene Chloride or acetone was added to it. PEG (Polyethylene glycol) was added to it with constant stirring.

Example 4

The compressed tablets were evaluated against the following assigned parameters.

Hardness:

The resistance of the tablet to chipping, abrasion, or breakage under the conditions of storage transportation and handling before usage depends on its hardness. Hardness of the tablet of each formulation was determined using Monsanto hardness tester. The hardness of controlled release tablets is generally kept higher than conventional tablets as increased hardness delays the disintegration of the tablet. A hardness of about 6-20 kg/cm$^2$ is considered to be satisfactory for CR tablets. Results showed a hardness value of 6.43±0.01 kg/cm$^2$.

Thickness:

The thickness and diameter of the tablets was determined using a Micrometer screw-gauge. Five tablets from each type of formulation were used and average values were calculated and determined to be 6.20 to 6.90 mm for elongated tablets of 800 mg and 5.27 to 6.20 mm for elongated bi-convex tablets of 600 mg.

Example 5

Friability:

Friability is the loss of weight of tablet in the container due to removal of fine particles from the surface. Friability test is carried out to access the ability of the tablet to withstand abrasion in packaging, handling and transport. Roche friabilator was employed and consists of a plastic chamber that revolves at 25 rpm while dropping the tablets from a height of 6 inches in each revolution. Pre-weighed sample of tablets was placed in the friabilator and were subjected to 100 revolutions. Tablets were de-dusted utilizing a soft muslin cloth and reweighed, the loss in the weight of tablet is the measure of friability and is expressed in percentage as % Friability=loss in weight/initial weight× 100. Results gave a value of 0.73±0.01.

Variation in Weight:

USP weight variation test was done by weighing 20 tablets individually; calculating the average weight and comparing the individual tablet weight to the average weight variation tolerance. Results showed a variation value of 0.903±0.01.

Content Uniformity:

Ten randomly selected tablets were weighed and the average weight was calculated. The tablets were powdered in a glass mortar. The weight equivalent to tablet was weighed. The weighed amount was dissolved in a solvent system in a separate volumetric flask using magnetic stirrer, the volume was adjusted with 0.1N HCl and the solution was filtered. Aliquots of this solution are diluted with 0.1N HCl in separate volumetric flasks in Lambert's-Beer's Range. The drug content in formulation is determined spectrophotometrically. Results show 99.31±0.12% of the drug was present in the formulation.

Example 6

Dissolution Study

The cumulative dissolution of the tablets was investigated in vitro using the apparatus II of U.S. Pharmacopoeia. One tablet to be dissolved was placed in each of the six vessels. Dissolution studies were carried out using 900 mL of phosphate buffer (pH 6.8) USP, as dissolution fluid in USP paddle type apparatus, maintaining a paddle rotational speed of 60 rpm at 37° C. (EXAMPLES 10-16) or under the same conditions but using a phosphate buffer at pH 7.4 (EXAMPLES 17-18, and 20). Samples (10 ml) were withdrawn at hourly intervals and each withdrawn sample was replaced with fresh buffer.

Standard solution—Drug (22.4 mg) was dissolved in 2 mL of methanol (AR) and the volume was made up to 100 mL in volumetric flask with phosphate buffer (pH 6.8) (EXAMPLES 10-16) or phosphate buffer (pH 7.4) (EXAMPLES 17-18 and 20). Ten mL of this solution was further diluted to 100 ml with phosphate buffer (pH 6.8) (EXAMPLES 10-16) or phosphate buffer (pH 7.4) (EXAMPLES 17-18 and 20) to yield a concentration of 22.4 µg/mL. Absorbance of the solution was measured at 293 nm in duplicate using 1 cm cuvette.

Example 7

Sample preparation—At specific time points of dissolution, 10 ml aliquot of sample was withdrawn and filtered through Whatman Filter no 1 while discarding 5 ml of initial filtrate. Two ml of the solution was diluted to 50 ml with phosphate buffer (pH 6.8) (EXAMPLES 10-16) or phosphate buffer (pH 7.4) (EXAMPLES 17-18 and 20) and absorbance was measured at 293 nm against phosphate buffer (pH 6.8) blank.

Composition of various flavoxate formulations made by the inventors, including dosage forms of 400, 600 and 800 mg as well as elongate or round biconvex shapes have been listed below followed by their dissolution rates in vitro.

Example 8

Composition ranges of components of dose variants are provided in the following table

TABLE 5

| FLAVOXATE HCL 400/600/800 mg CR TABLET | | |
|---|---|---|
| S.No. | Ingredients | Range Qty/Tab. |
| 1 | Flavoxate HCL | 82% |
| 2 | HPMC K4M | 0.5 to 5% |
| 3 | HPMC K15M | 8-15% |
| 4 | HPMC K100M | 0.5-2% |
| 5 | PVP K30 | 4-6% |
| 6 | Lactose | 0 to 5% |
| 7 | Magnesium Stearate | 0.8-1% |
| 8 | Talc | 1-3% |
| 9 | Coll. Silica | Up to 1% |
| 10 | Isopropyl Alcohol | q.s. |

Table 6 provides the dissolution ranges of flavoxate formulations prepared with above mentioned composition.

TABLE 6

| Dissolution Profile | |
|---|---|
| Time (hours) | Dissolution Range (%) |
| 1 | 5-30 |
| 2 | 20-35 |
| 4 | 25-50 |
| 6 | 30-55 |
| 8 | 45-85 |
| 24 | Not less than 85 |

Example 9

The weight of polymer, bonder, excipients of an exemplary 800 mg flavoxate controlled release (CR) tablet along with the dissolution profile over time are depicted in the following table and FIG. 1A.

TABLE 7

| Flavoxate hydrochloride controlled release tablets 800 mg. | | | |
|---|---|---|---|
| Exp.-D | | | |
| Intended Avg. Weight 950 mg B. Size: 500 Tablets Hardness: 9-10 kg/cm² Thickness: 6.69 mm to 6.80 mm | | Film Coated Tablets Description: White, elongated, controlled release film coated tablets Identification: Positive for Flavoxate Hydrochloride EP Avg. weight: 958.3 mg | |
| Ingredient | Qty./Tab | Time | % age Drug Released |
| Flavoxate Hydrochloride EP | 800 mg | 1 hr | |
| HPMC K15M | 80 mg | 2 hrs | 22.45 |
| PVP K30 | 40 mg | 3 hrs | 28.44 |
| Isopropyl Alcohol IP | q.s. | 4 hrs | 34.66 |

TABLE 7-continued

| Flavoxate hydrochloride controlled release tablets 800 mg. | | | | |
|---|---|---|---|---|
| Magnesium stearate IP | 8 mg | 5 hrs | | 49.24 |
| Colloidal Silicon Dioxide IP | 8 mg | 6 hrs | | 58.33 |
| Lactose IP | 8 mg | 7 hrs | | 62.21 |
| HPMC K100M | 6 mg | 8 hrs | | 71.92 |
| | | 9 hrs | | 74.39 |
| | | 10 hrs | | 77.97 |
| | | 12 hrs | | 83.89 |
| | | 14 hrs | | 88.78 |
| | | 16 hrs | | 91.94 |
| | | 24 hrs | | 99.90 |

Example 10

Figure 1B:
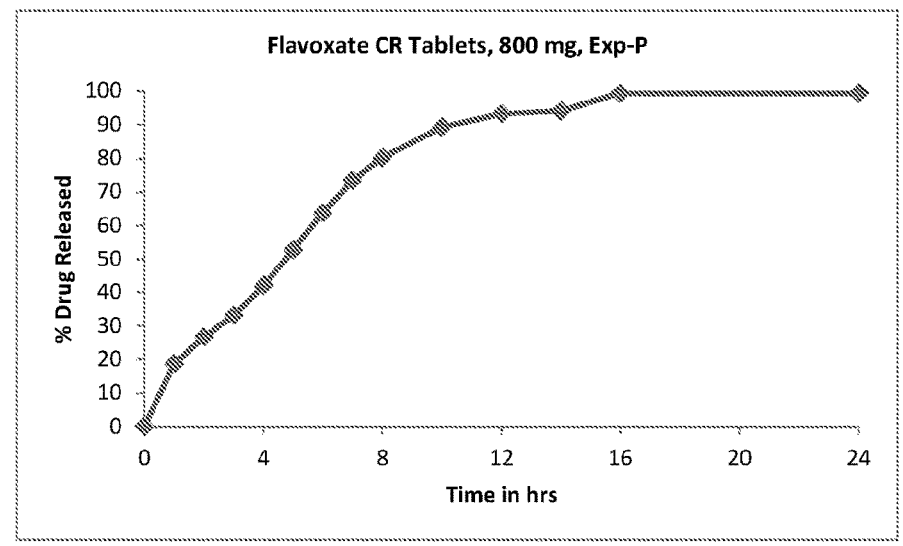

The weight of polymer, binder, excipients of an exemplary 800 mg flavoxate controlled release (CR) tablet along with the dissolution profile over time are depicted in the following table and FIG. 1B.

TABLE 8

| Exp.-P | | | |
|---|---|---|---|
| Intended Avg. Weight 972 mg | | Film coated Tablets | |
| B. Size: 500 Tablets | | Description: White, elongated, | |
| Hardness: 6-7 kg/cm² | | controlled release uncoated tablets | |
| Thickness: 6.33 mm to 6.39 mm | | Identification: Positive for | |
| | | Flavoxate Hydrochloride EP | |
| | | Avg. weight: 982.2 mg | |
| Ingredient | Qty./Tab | Time | % age Drug Released |
| Flavoxate Hydrochloride EP | 800 mg | | — |
| HPMC K15M | 100 mg | 1 hr | 18.68 |
| PVP K30 | 50 mg | 2 hrs | 26.70 |
| Isopropyl Alcohol IP | q.s. | 3 hrs | 33.11 |
| Magnesium Stearate IP | 10 mg | 4 hrs | 41.95 |
| Colloidal Silicon Dioxide IP | 4 mg | 5 hrs | 52.82 |
| HPMC K100M | 8 mg | 6 hrs | 63.73 |
| | | 7 hrs | 73.35 |
| | | 8 hrs | 80.22 |
| | | 10 hrs | 89.26 |
| | | 12 hrs | 93.25 |
| | | 14 hrs | 94.17 |
| | | 16 hrs | 99.31 |
| | | 24 hrs | 99.31 |

Example 11

Figure 1C:
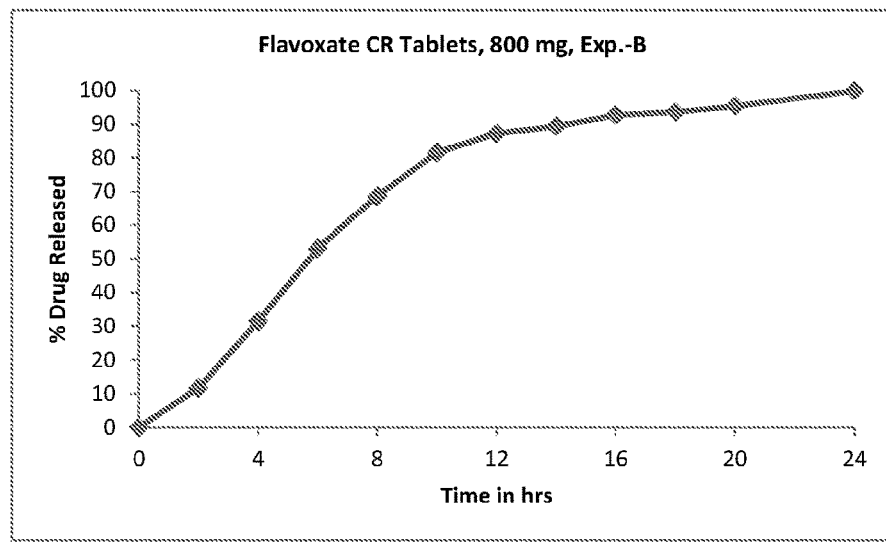

The weight of polymer, binder, excipients of an exemplary 800 mg flavoxate controlled release (CR) tablet along with the dissolution profile over time are depicted in the following table and FIG. 1C.

TABLE 9

| Exp.-B | | | |
|---|---|---|---|
| Intended Avg. Weight 1025 mg | | Film Coated Tablets | |
| B. Size: 3300 Tablets | | Description: White, elongated, | |
| Hardness: 8-9 kg/cm² | | controlled release film coated tablets | |
| Thickness: 6.91 mm to 6.97 mm | | Identification: Positive for Flavoxate | |
| | | Hydrochloride EP | |
| | | Avg. weight: 1044.1 mg | |
| Ingredient | Qty./Tab | Time | % age Drug Released |
| Flavoxate Hydrochloride EP | 800 mg | 1 hr. | |
| HPMC K15M | 140 mg | 2 hrs | 11.68 |
| PVP K30 | 45 mg | 4 hrs | 31.47 |
| Isopropyl Alcohol IP | q.s. | 6 hrs | 53.00 |

TABLE 9-continued

| Magnesium Stearate IP | 10 mg | 8 hrs | 68.59 |
|---|---|---|---|
| Talc IP | 30 mg | 10 hrs | 81.63 |
| | | 12 hrs | 87.24 |
| | | 14 hrs | 89.40 |
| | | 16 hrs | 92.66 |
| | | 18 hrs | 93.61 |
| | | 20 hrs | 95.38 |
| | | 24 hrs | 99.90 |

Example 12

Figure 1D:
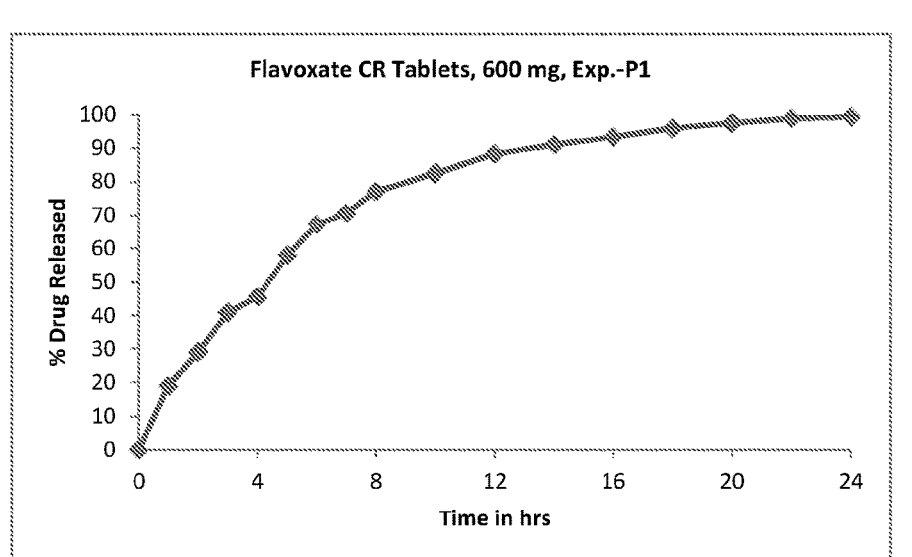

The weight of polymer, binder, excipients of an exemplary 600 mg flavoxate controlled release (CR) tablet along with the dissolution profile over time are depicted in the following table and FIG. 1D.

TABLE 10

| Exp-P1 | | Drug Release Pattern | |
|---|---|---|---|
| Intended Avg. Weight 730 mg | | Film Coated Tablets | |
| B. Size: 3000 Tablets | | Description: White, elongated | |
| Hardness: 9 kg/cm² | | controlled release film coated | |
| Thickness: 5.87 mm | | tablets | |
| | | Identification: Positive for | |
| | | Flavoxate Hydrochloride EP | |
| | | Diameter: 5.87 mm | |
| Ingredient | Qty./Tab | Time | % age Drug Released |
| Flavoxate Hydrochloride EP | 600 mg | | |
| HPMC K15M | 75 mg | 1 hr | 19.05 |
| PVP K30 | 37.5 mg | 2 hrs | 29.12 |
| Isopropyl alcohol IP | q.s. | 3 hrs | 40.93 |
| Magnesium Stearate IP | 7.5 mg | 4 hrs | 45.62 |
| Colloidal silicon dioxide IP | 3 mg | 5 hrs | 57.91 |
| HPMC K100M | 6 mg | 6 hrs | 67.15 |
| | | 7 hrs | 70.61 |
| | | 8 hrs | 77.01 |
| | | 10 hrs | 82.51 |
| | | 12 hrs | 88.32 |
| | | 14 hrs | 91.09 |
| | | 16 hrs | 93.29 |
| | | 18 hrs | 95.91 |
| | | 20 hrs | 97.49 |
| | | 22 hrs | 98.84 |
| | | 24 hrs | 99.30 |

Example 13

Figure 1E:
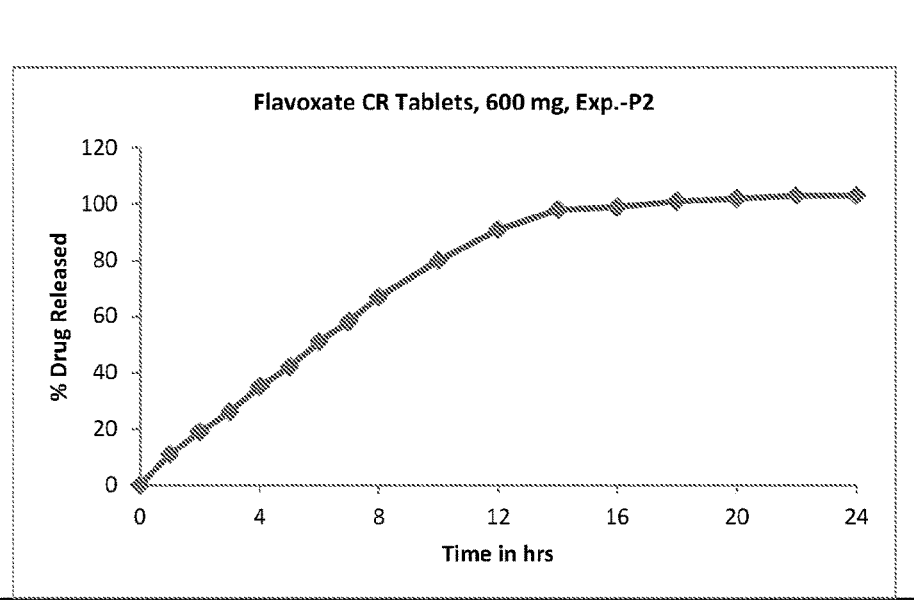

The weight of polymer, binder, excipients of an exemplary 600 mg flavoxate controlled release (CR) tablet along with the dissolution profile over time are depicted in the following table and FIG. 1E.

TABLE 11

| Exp-P2 | | | Drug Release Pattern |
|---|---|---|---|

| Intended Avg. Weight 730 mg<br>B. Size: 3000 Tablets<br>Hardness: 15 kg/cm$^2$<br>Thickness: 5.96 mm | | | Film Coated Tablets<br>Description: White, elongated bi-<br>convex release film coated tablets<br>Identification: Positive for<br>Flavoxate Hydrochloride EP<br>Diameter: 5.87 mm |
|---|---|---|---|
| Ingredient | Qty./Tab | Time | % age Drug Released |
| Flavoxate Hydrochloride EP | 600 mg | | |
| HPMC K15M | 75 mg | 1 hr | 11 |
| PVP K30 | 37.5 mg | 2 hrs | 19 |
| Isopropyl alcohol IP | q.s. | 3 hrs | 26 |
| Magnesium Stearate IP | 7.5 mg | 4 hrs | 35 |
| Colloidal silicon dioxide IP | 3 mg | 5 hrs | 42 |
| HPMC K100M | 6 mg | 6 hrs | 51 |
| | | 7 hrs | 58 |
| | | 8 hrs | 67 |
| | | 10 hrs | 80 |
| | | 12 hrs | 91 |
| | | 14 hrs | 98 |
| | | 16 hrs | 99 |
| | | 18 hrs | 101 |
| | | 20 hrs | 102 |
| | | 22 hrs | 103 |
| | | 24 hrs | 103 |

Example 14

Figure 1F:
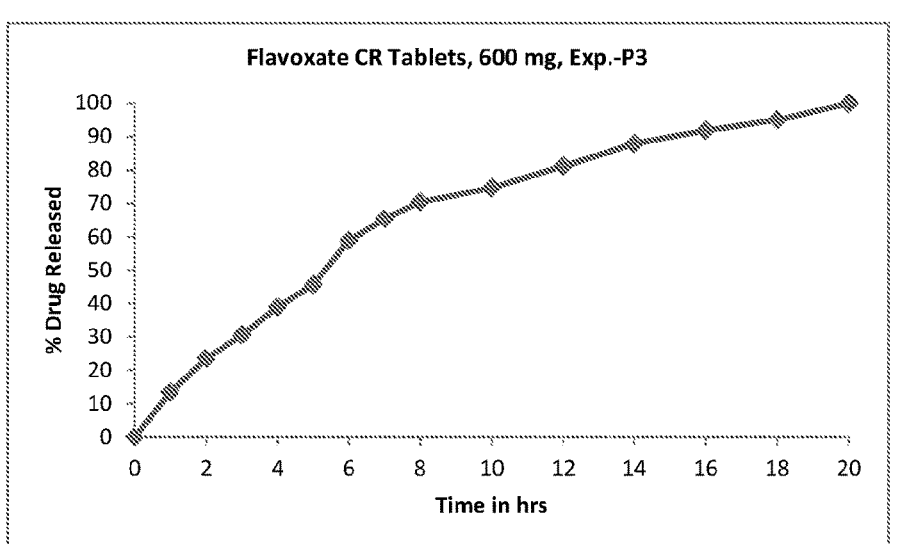

The weight of polymer, binder, excipients of an exemplary 600 mg flavoxate controlled release (CR) tablet along with the dissolution profile over time are depicted in the following table and FIG. 1F.

TABLE 12

| Exp-P3 | | | Drug Release Pattern |
|---|---|---|---|

| Intended Avg. Weight 730 mg<br>B. Size: 3000 Tablets<br>Hardness: 15 kg/cm$^2$<br>Thickness: 5.96 mm | | | Film Coated Tablets<br>Description: White, elongated bi-<br>convex release film coated tablets<br>Identification: Positive for<br>Flavoxate Hydrochloride EP<br>Diameter: 5.87 mm |
|---|---|---|---|
| Ingredient | Qty./Tab | Time | % age Drug Released |
| Flavoxate Hydrochloride EP | 600.00 mg | | |
| HPMC K4M | 14.60 mg | 1 hr | 13.5 |
| HPMC K15M | 43.80 mg | 2 hrs | 23.4 |
| Lactose | 18.80 mg | 3 hrs | 30.5 |
| PVP K30 | 36.50 mg | 4 hrs | 38.9 |
| Isopropyl alcohol IP | q.s. | 5 hrs | 45.6 |
| Magnesium Stearate IP | 7.30 mg | 6 hrs | 58.9 |
| Colloidal silicon dioxide IP | 3.00 mg | 7 hrs | 65.4 |
| HPMC K100M | 6.00 mg | 8 hrs | 70.5 |
| | | 10 hrs | 74.7 |
| | | 12 hrs | 81.2 |
| | | 14 hrs | 87.9 |
| | | 16 hrs | 91.9 |
| | | 18 hrs | 95.0 |
| | | 20 hrs | 99.9 |

Example 15

Figure 1G:
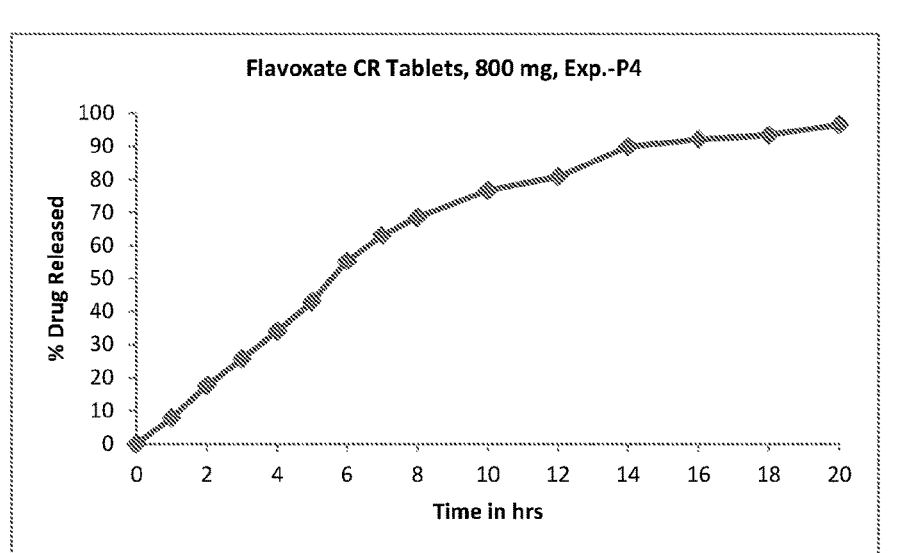

The weight of polymer, binder, excipients of an exemplary 800 mg flavoxate controlled release (CR) tablet along with the dissolution profile over time are depicted in the following table and FIG. 1G.

TABLE 13

| Exp-P4 | | | Drug Release Pattern |
|---|---|---|---|

| Intended Avg. Weight 987 mg<br>B. Size: 3000 Tablets<br>Hardness: 17 kg/cm$^2$<br>Thickness: 6.12 mm | | | Film Coated Tablets<br>Description: White, elongated bi-<br>convex release film coated tablets<br>Identification: Positive for<br>Flavoxate Hydrochloride EP<br>Diameter: 5.87 mm |
|---|---|---|---|
| Ingredient | Qty./Tab | Time | % age Drug Released |
| Flavoxate Hydrochloride EP | 800.00 mg | | |
| HPMC K4M | 19.46 mg | 1 hr | 7.87 |
| HPMC K15M | 58.40 mg | 2 hrs | 17.62 |
| Lactose | 25.06 mg | 3 hrs | 25.66 |
| PVP K30 | 48.66 mg | 4 hrs | 34.04 |
| Isopropyl alcohol IP | q.s. | 5 hrs | 42.91 |
| Magnesium Stearate IP | 9.73 mg | 6 hrs | 55.26 |
| Colloidal silicon dioxide IP | 4.00 mg | 7 hrs | 63.14 |
| HPMC K100M | 8.00 mg | 8 hrs | 68.51 |
| | | 10 hrs | 76.7 |
| | | 12 hrs | 80.88 |
| | | 14 hrs | 89.85 |
| | | 16 hrs | 92.06 |
| | | 18 hrs | 93.39 |
| | | 20 hrs | 96.52 |

Example 16

U.S. Pat. No. 5,165,937 discloses the use of hydrophilic polymer derived from cellulose such as hydroxypropylmethylcellulose (HPMC), and the preferential use of binder, polyvinyl alcohol (PVA) in controlled release formulations containing flavoxate hydrochloride. U.S. Pat. No. 5,165,937 also teaches that an acidifying agent is an essential ingredient for ensuring the solubility and stability of controlled release flavoxate formulations.

We undertook several formulation trials with acidifying agent and following the aqueous wet granulation manufacturing process as disclosed in U.S. Pat. No. 5,165,937. We observed that the granulation end point was difficult to achieve and, as a result, caused significant reproducibility concerns. Moreover, the resulting finished product had an unacceptable mottled appearance.

To establish whether the acidifying agent in the formulation disclosed in U.S. Pat. No. 5,165,937 was indeed essential, we compared a dissolution profile of that formulation without acidifying agent in pH 7.4 to a representative formulation of the present invention. As shown in Table 14, without acidifying agent, dissolution of the U.S. Pat. No. 5,165,937 formulation was almost negligible in the first 8 hours, establishing that the acidifying agent really is essential to that formulation. In contrast, a representative formulation of the present invention without acidifying agent shows significantly higher drug release over the same period.

TABLE 14

| | % Flavoxate Drug dissolution in pH 7.4 | |
|---|---|---|
| Time in hrs | Representative Embodiment of the Invention | Representative formulation from U.S. Pat. No. 5,165,937 (without acidifying agent) |
| 1 | 7 | 1 |
| 2 | 12 | 1 |
| 3 | 18 | 2 |
| 4 | 25 | 2 |
| 5 | 30 | 3 |

TABLE 14-continued

| | % Flavoxate Drug dissolution in pH 7.4 | |
|---|---|---|
| Time in hrs | Representative Embodiment of the Invention | Representative formulation from U.S. Pat. No. 5,165,937 (without acidifying agent) |
| 6 | 34 | 3 |
| 7 | 37 | 4 |
| 8 | 46 | 4 |

Example 17

Figure 4:
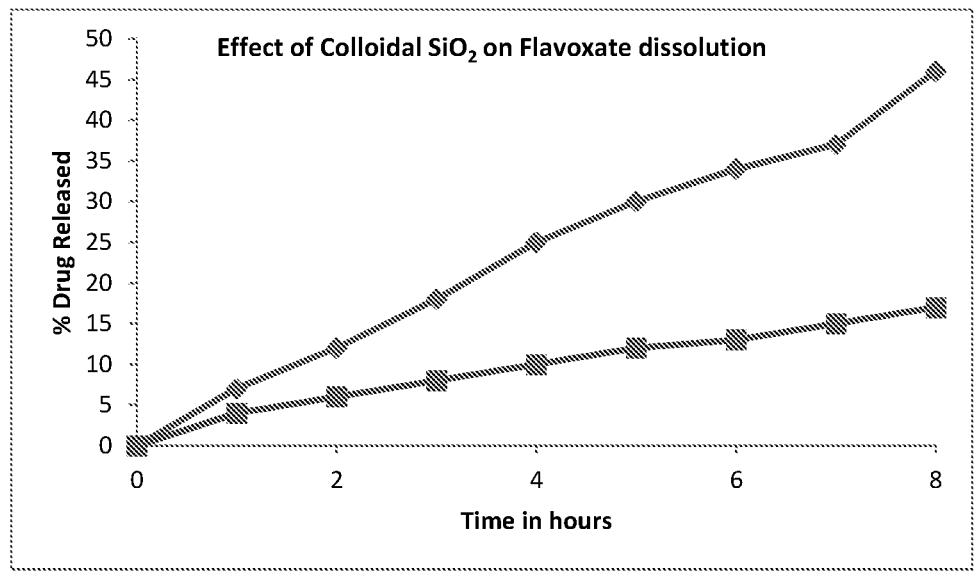
FIG. 4 depicts the effect of colloidal $SiO_2$ on flavoxate dissolution; wherein X-axis represents % drug released and Y-axis represent time in hours.
Figure 5:
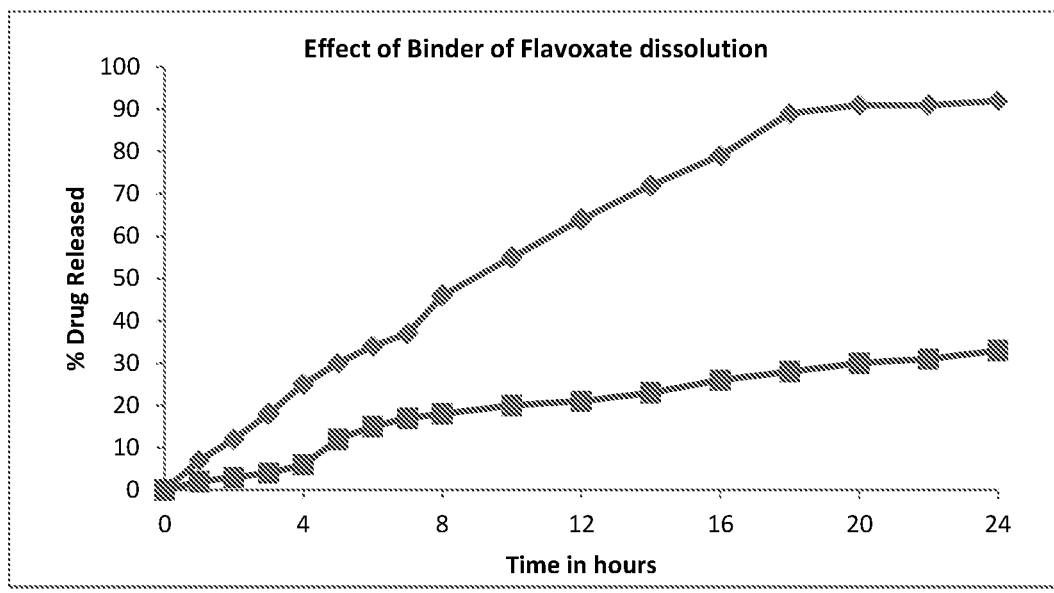
FIG. 5 depicts the effect of PVK-30 compared to PVA on flavoxate dissolution; wherein X-axis represents % drug released and Y-axis represent time in hours.

As noted above, additionally improved drug release in basic with environment was unexpectedly achieved by including colloidal silicon dioxide and/or the polyvinylpyrrolidone, PVP K-30 into the composition of the invention. This is evident from studies undertaken to evaluate with and without colloidal silicon dioxide (FIG. 4) and in another set of studies evaluating polyvinyl alcohol (PVA) as a binder in place of PVP K-30 (FIG. 5).

The weight of polymer, binder, and excipients of 600 mg flavoxate controlled release (CR) tablets used for these studies (A-C) is provided in Table 15.

TABLE 15

| Ingredient | A (Qty./Tab) | B (Qty./Tab) | C (Qty./Tab) |
|---|---|---|---|
| Flavoxate Hydrochloride | 600.00 mg | 600.00 mg | 600.00 mg |
| HPMC K15M | 75 mg | 75 mg | 75 mg |
| PVP K30 | 37.5 mg | 37.5 mg | — |
| Polyvinyl Alcohol (PVA) | — | — | 37.5 mg |
| Isopropyl alcohol | q.s. | q.s. | q.s. |
| HPMC K100M | 6 mg | 6 mg | 6 mg |
| Magnesium Stearate | 7.5 mg | 7.5 mg | 7.5 mg |
| Colloidal silicon dioxide | 3 mg | — | 3 mg |

A. Tablet with Colloidal Silicon Dioxide and PVP K30M (Exp-P2)

Controlled-release tablets were made by sifting and mixing together dry flavoxate hydrochloride and HPMC K15M. This mixture was granulated using PVP K30 solution in isopropyl alcohol, then dried to a limit of detection (LOD) of less than 2% at 45-50° C. The dried granules were milled and sized, then mixed with sifted HPMC K100M, colloidal silicon dioxide, and magnesium stearate. Tablets were compressed, then coated with coating dispersion (% by weight): opadry white (3.32%), PEG 6000 (0.50%), isopropyl alcohol (27.4%), and methylene chloride (68.82%). The tablets were evaluated for dissolution in 900 mL pH 7.4 phosphate buffer at 60 rpm. Results are shown (compared to other formulations) in FIG. 4 and FIG. 5.

B. Tablet without Colloidal Silicon Dioxide

Controlled-release tablets were made by sifting and mixing together dry flavoxate hydrochloride and HPMC K15M. This mixture was granulated using PVP K30 solution in isopropyl alcohol, then dried to a limit of detection (LOD) of less than 2% at 45-50° C. The dried granules were milled and sized, then mixed with sifted HPMC K100M and magnesium stearate. Tablets were compressed, then coated with coating dispersion (% by weight): opadry white (3.32%), PEG 6000 (0.50%), isopropyl alcohol (27.4%), and methylene chloride (68.82%). The tablets were evaluated for dissolution in 900 mL pH 7.4 phosphate buffer at 60 rpm. Results, including a comparison to a formulation comprising colloidal silicon dioxide, are shown in FIG. 4.

C. Tablet with PVA

Controlled-release tablets were made by sifting and mixing together dry flavoxate hydrochloride, polyvinyl alcohol (PVA), and HPMC K15M. This mixture was granulated using isopropyl alcohol, then dried to a limit of detection (LOD) of less than 2% at 45-50° C. The dried granules were milled and sized, then mixed with sifted HPMC K100M, colloidal silicon dioxide, and magnesium stearate. Tablets were compressed, then coated with coating dispersion (% by weight): opadry white (3.32%), PEG 6000 (0.50%), isopropyl alcohol (27.4%), and methylene chloride (68.82%). The tablets were evaluated for dissolution in 900 mL pH 7.4 phosphate buffer at 60 rpm. Results, including a comparison to a formulation comprising colloidal silicon dioxide, are shown in FIG. 5.

Example 18

As discussed above, the release profile of controlled release (CR) formulations depends on a variety of factors that are not always predictable. With delayed or CR tablets, care must be taken to avoid release of the active ingredient in an uncontrolled manner because such "dose-dumping" may cause serious adverse effects.

There is a subgroup of patients who are vulnerable to accidental overdose through concomitant consumption of alcoholic beverages with modified release medications. Thus in vitro testing for alcohol-induced undermining of sustained release characteristics is advisable as a routine characterization test.

As controlled release of flavoxate is modulated by a polymer matrix, dose dumping may occur if the release control is compromised through dissolution of the controlling agent in hydro-alcoholic liquids. In particular, the formulations of the invention contain significantly increased dosages of flavoxate hydrochloride as compared to the currently commercially available immediate release compositions. As a result, there is a much higher risk of safety issues and adverse events due to exposure to high drug levels if the release controls of the formulations are compromised. A similarly increased risk exists if the formulation of U.S. Pat. No. 5,165,937 were to be compromised.

Figure 6:
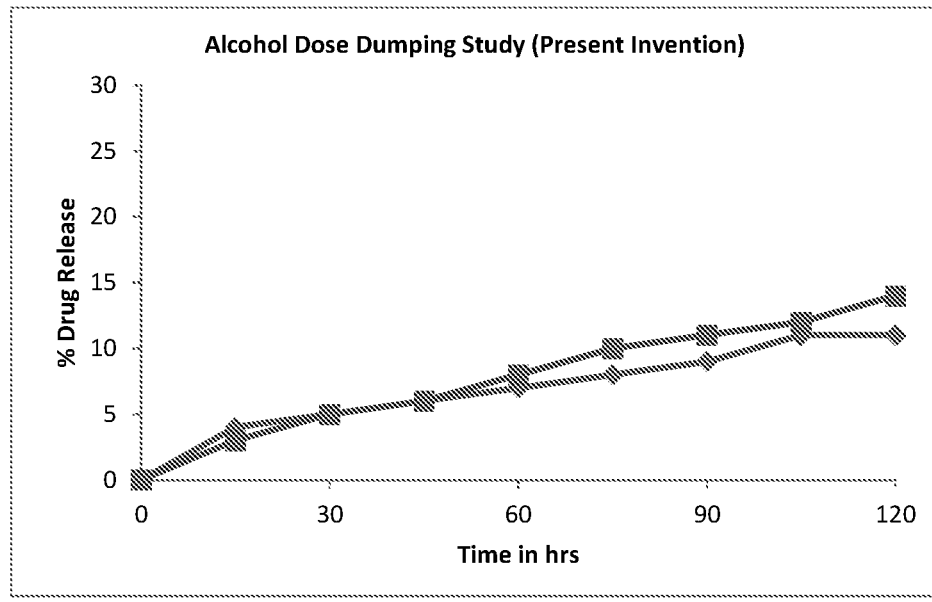
FIG. 6 depicts the results of an alcohol dose dumping study for a representative formulation of the invention.
Figure 7:
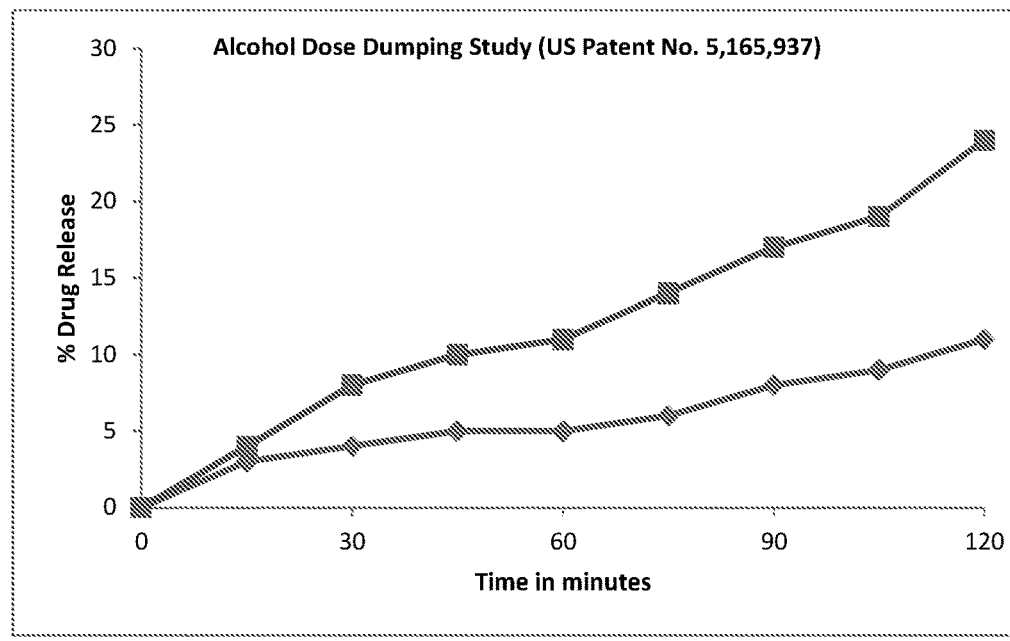
FIG. 7 depicts the results of an alcohol dose dumping study for a formulation as described in U.S. Pat. No. 5,165,937.

Experiments were conducted to evaluate the risk of ADD by a representative CR formulation of present invention (Exp-P2, described in EXAMPLE 14), as there can be a major risk of release the drug rapidly leading to safety issues and adverse events due to exposure to high drug levels than immediate release dosage required. Accordingly, both formulations (of U.S. Pat. No. 5,165,937 and the present invention) were evaluated in an 'Alcohol Dose Dumping study' using the in-vitro dissolution medium of 0.1 N HCl containing 0% and 40% ethanol. The results are shown in FIGS. 6 and 7, respectively.

Surprisingly, the results show that there is no difference in drug release in 0% and 40% alcohol media for the formulations of the present invention (FIG. 6), while the formulation of U.S. Pat. No. 5,165,937 shows significant drug release in 40% ethanol medium (FIG. 7).

Example 19

Comparative dissolution profiles of a representative embodiment of the present invention and of U.S. Pat. No. 5,165,937 were prepared as follows.

Representative controlled-release tablets of the present invention (Exp-P2, see EXAMPLE 14, EXAMPLE 18) were made by sifting and mixing together dry flavoxate hydrochloride and HPMC K15M. This mixture was granulated using PVP K30 solution in isopropyl alcohol, then dried to a limit of detection (LOD) of less than 2% at 45-50° C. The dried granules were milled and sized, then mixed with sifted HPMC K100M, colloidal silicon dioxide, and magnesium stearate. Tablets were compressed, then coated with coating dispersion (% by weight): opadry white (3.32%), PEG 6000 (0.50%), isopropyl alcohol (27.4%), and methylene chloride (68.82%).

Representative tablets (FT-03) of U.S. Pat. No. 5,165,937 were prepared by sifting and mixing together dry flavoxate hydrochloride and HPMC K15M. This mixture was granulated using polyvinyl alcohol solution in water, then dried to a water content of less than 3% at 50° C. The dried granules were milled and sized, then mixed with tartaric acid, talc, and magnesium stearate. Tablets were compressed, then coated with coating dispersion (% by weight): Methocel E 5 (HPMC) (5.7%), talc (7.4%), titanium dioxide (5.0%), saccharose (1.1%), PEG 6000 (1.0%), and water (79.6%).

The weight of polymer, binder, and excipients of the FT-03 tablets is provided in Table 16.

TABLE 16

| Ingredient | Qty./Tab |
| --- | --- |
| Flavoxate Hydrochloride | 600.00 mg |
| HPMC K15M | 60.00 mg |
| Polyvinyl Alcohol (PVA) | 29.65 mg |
| Magnesium Stearate | 6.25 mg |
| Tartaric Acid | 75.00 mg |
| Talc | 9.36 mg |

The tablets were evaluated for dissolution in 900 mL pH 7.4 phosphate buffer at 60 rpm. Results are shown in FIG. 8.

Example 20

Figure 9A:
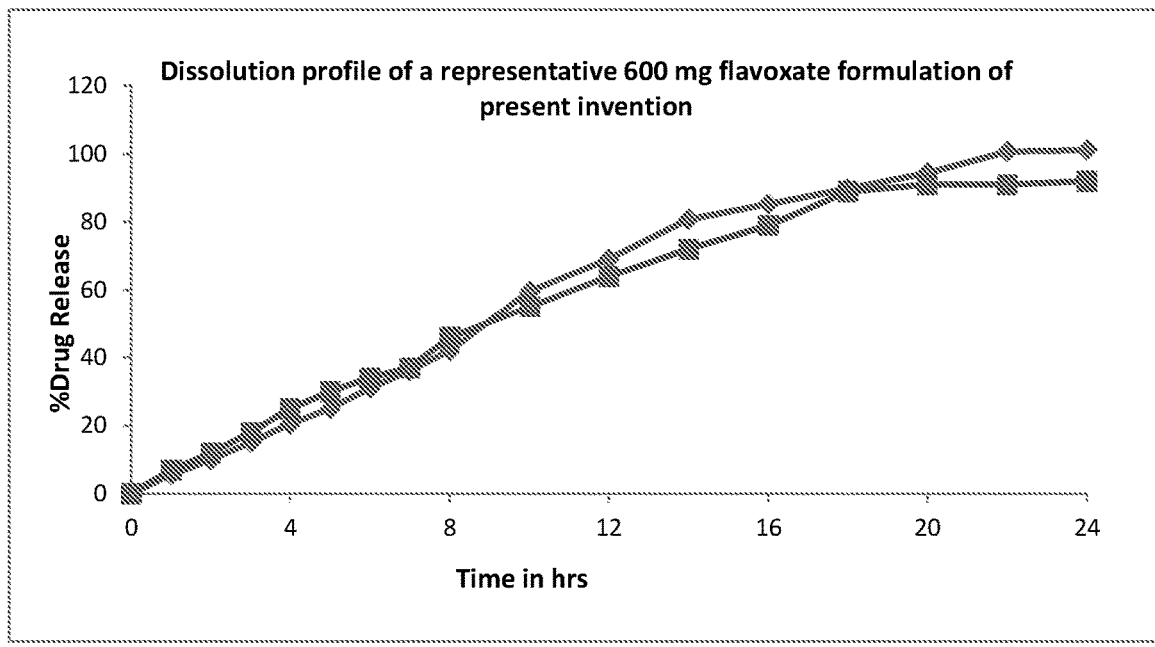
FIGS. 9A and 9B provide comparative dissolution of a representative 600 mg flavoxate formulation of present invention and prior art (U.S. Pat. No. 5,165,937)
Figure 9B:
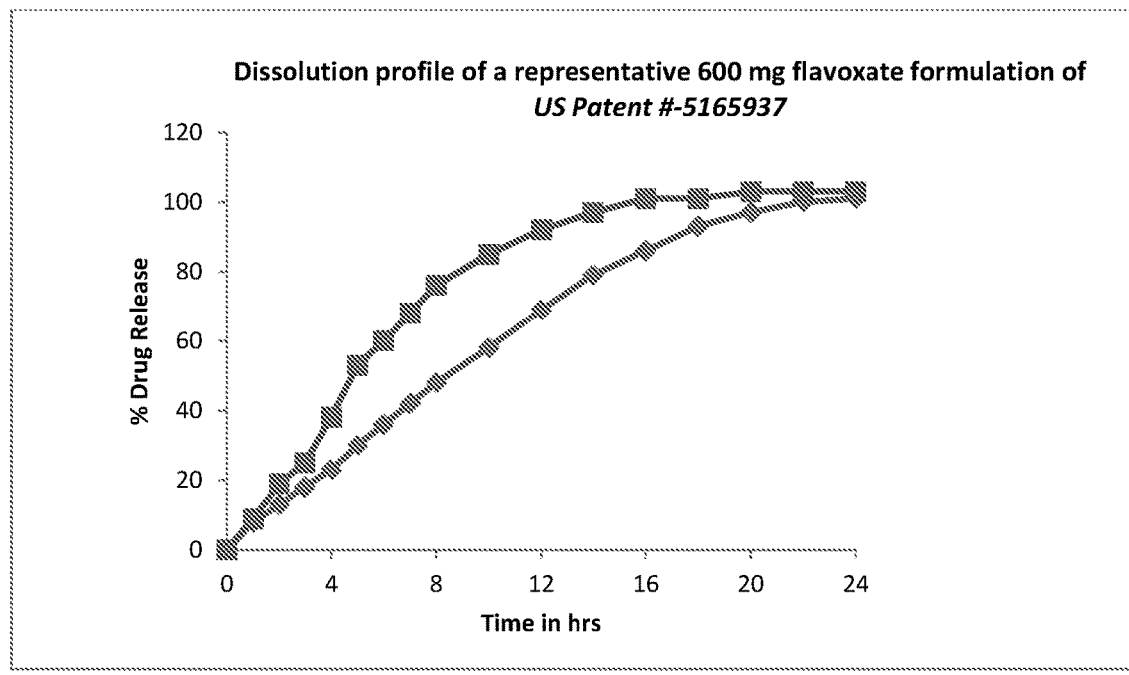
Figure 9C:
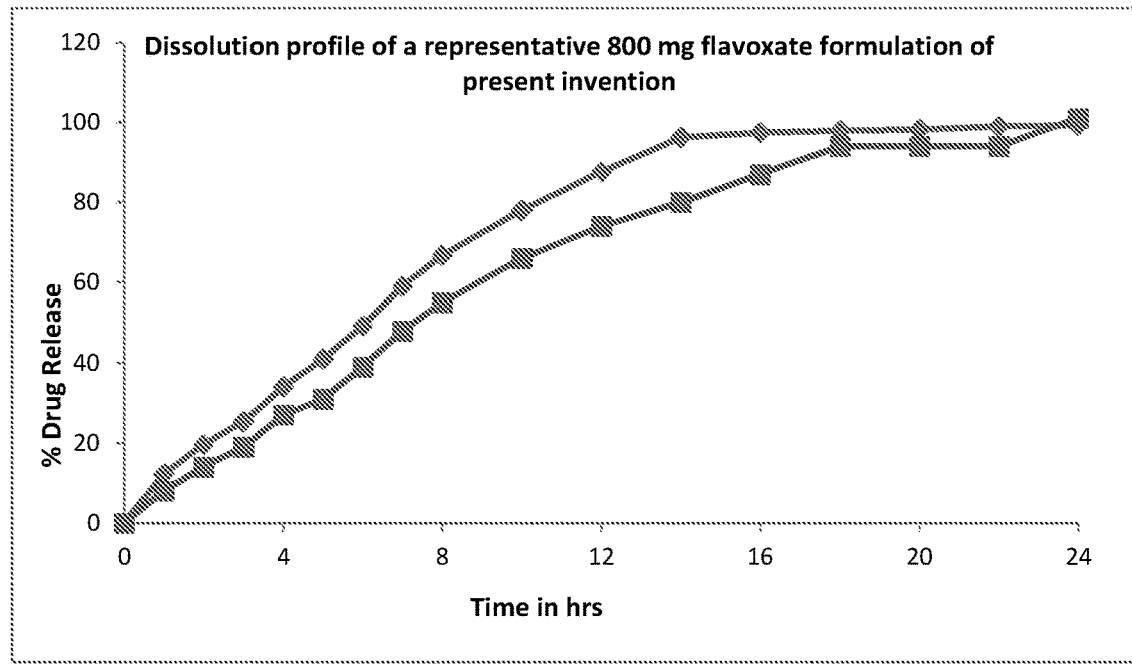
FIGS. 9C and 9D provide comparative dissolution of a representative 800 mg flavoxate formulation of the present invention and prior art (U.S. Pat. No. 5,165,937) at extremes of pH simulating physiological conditions of human GIT. The X-axis represents % drug released and Y-axis represents time in hours.
Figure 9D:
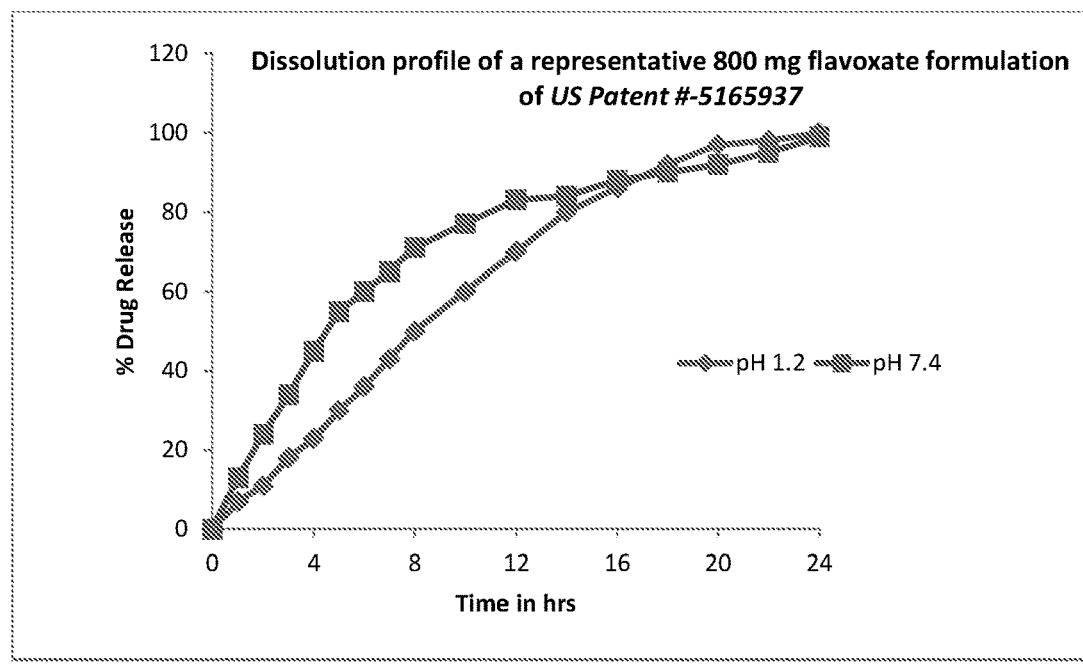

Additional experiments were conducted to illustrate comparative dissolution of 600 and 800 mg of flavoxate formulation of present invention and prior art (U.S. Pat. No. 5,165,937) at in vitro at extremes of pH simulating physiological conditions of human GIT. FIGS. 9A and 9B provide comparative dissolution of a representative 600 mg flavoxate formulation of present invention and prior art (U.S. Pat. No. 5,165,937); FIGS. 9C and 9D provide comparative dissolution of a representative 800 mg flavoxate formulation of the present invention and prior art (U.S. Pat. No. 5,165, 937).

Surprisingly, as the formulation of the present invention does not contain acidifying agent, there was no significant difference in flavoxate drug dissolution as evaluated in dissolution studies at pH 1.2 and 7.4. These data clearly demonstrate the steady and consistent release of flavoxate salt from the formulation of the present invention at both extreme pHs for 24 hours. Thus the formulation of present invention is promising for pH-independent, controlled release of flavoxate drug throughout the human GIT.

Example 21

Figure 10A:
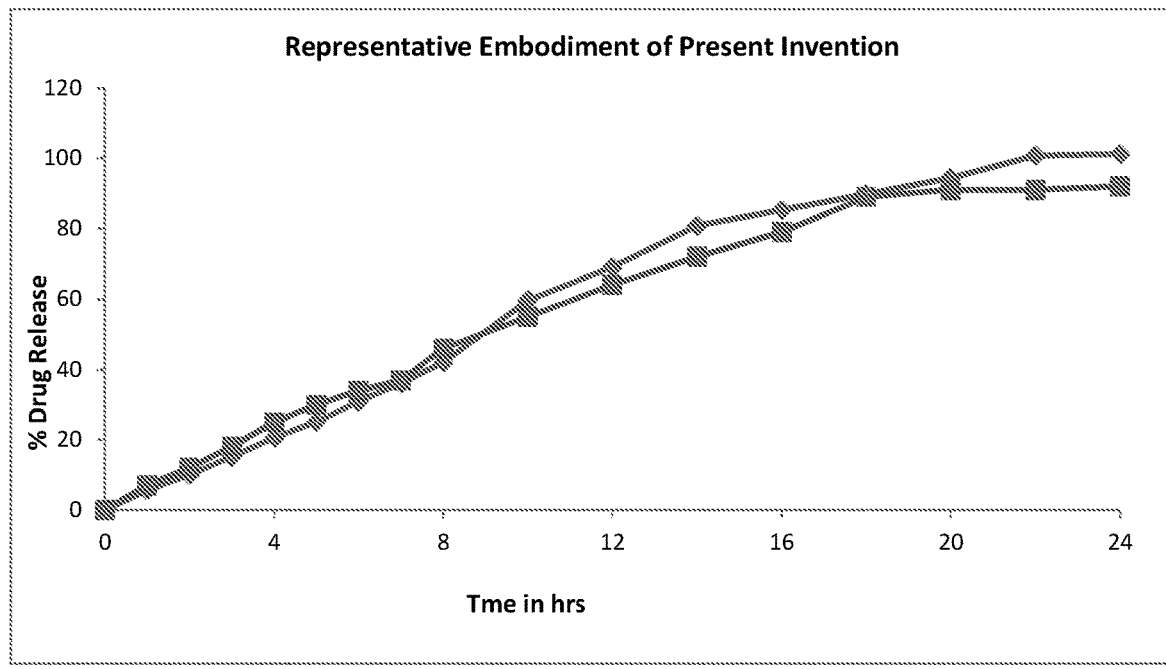
FIGS. 10A and 10B provide comparative dissolution of flavoxate formulation of present invention and prior art (U.S. Pat. No. 5,165,937) composition without acidifying agent at extremes of pH simulating physiological conditions of human GIT. The X-axis represents % drug released and Y-axis represents time in hours.
Figure 10B:
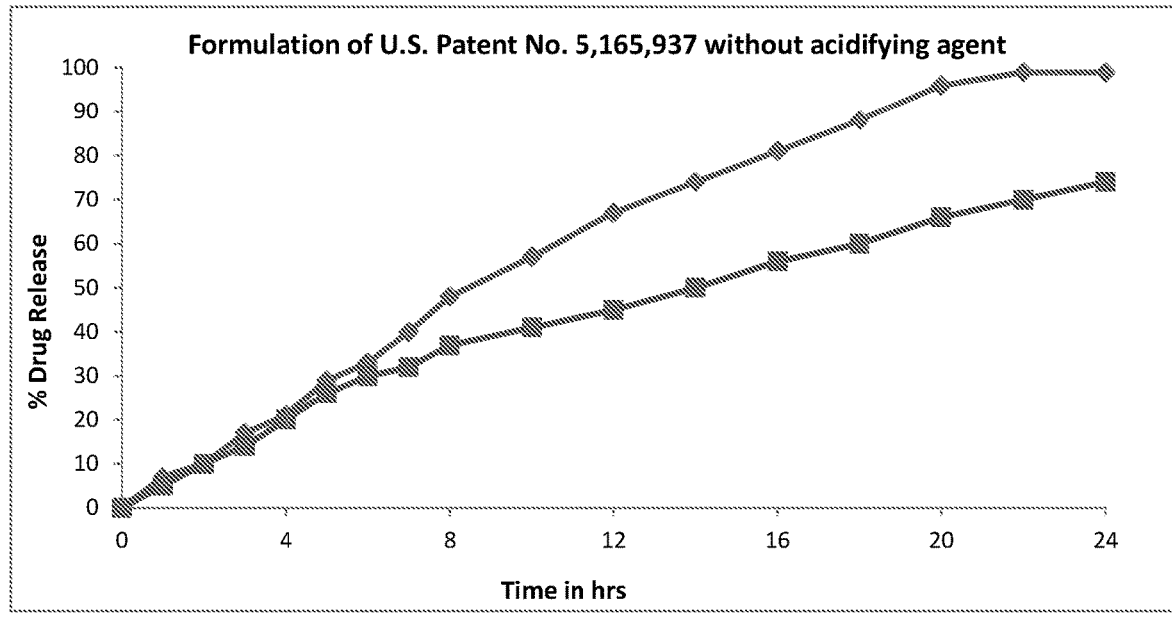

FIGS. 10A and 10B compare the dissolution profiles of a representative flavoxate formulation of present invention and a representative flavoxate formulation of U.S. Pat. No. 5,165,937 without an acidifying agent, at extremes of pH in vitro that simulate physiological conditions of the human GIT. FIG. 10A represents the effect of pH on dissolution rate of a flavoxate formulation of present invention and FIG. 10B represents the effect of pH on dissolution rate of the prior art flavoxate formulation without any acidifying agent.

As noted above, there was no significant difference in flavoxate drug dissolution as evaluated in dissolution studies at pH 1.2 and 7.4. This is in stark contrast to the effect of pH on the formulation of U.S. Pat. No. 5,165,937 lacking an acidifying agent, which showed much slower dissolution in pH 7.4 compared to pH 1.2. Thus, the present invention, which also lacks an acidifying agent, exhibits an unexpected pH-independent controlled release profile.

Example 22

As is known in the art, Bioavailability (BA) and Bioequivalence (BE) studies play a major role in the development of new drug (and their products or formulation) and their generic equivalents. BA is defined as the rate and extent to which the active ingredient or active moiety is absorbed from a drug product and becomes available at the site of action. For drug products that are not intended to be absorbed into the bloodstream, BA may be assessed by measurements intended to reflect the rate and extent to which the active ingredient or active moiety becomes available at the site of action. BE is defined as the absence of a significant difference in the rate and extent to which the active ingredient or active moiety in pharmaceutical equivalents or pharmaceutical alternatives becomes available at the site of drug action when administered at the same molar dose under similar conditions in an appropriately designed study.

Hence, further experiments were conducted to study the in vivo BA and BE of the flavoxate drug of the formulation of present invention. The formulation releases at least 10-15% of the flavoxate salt within 1 hour, achieves plasma concentrations greater than or equal to 1 mcg/ml and the rest of the drug releases flavoxate salt over 24 hours, achieves plasma concentrations of 1 mcg/ml for 24 hours.

The formulation achieves greater than or equal to 1 mcg/ml plasma concentrations of the metabolite of Flavoxate i.e. 3-methylflavone-8-carboxylic acid (MFCA) at about 1 hour and no later than two and a half hours. Typically the formulation achieves greater than or equal to 1 mcg/ml plasma concentrations of the metabolite of Flavoxate i.e. 3-methylflavone-8-carboxylic acid (MFCA) at about two hours.

Although the subject matter has been described herein with reference to certain preferred embodiments thereof, other embodiments are possible. As such, the spirit and scope of the appended claims should not be limited to the description of the preferred embodiment contained therein. It will be obvious to those skilled in the art to make various changes, modifications and alterations to the invention described herein. To the extent that these various changes, modifications and alteration do not depart from the scope of the present invention, they are intended to be encompassed therein.

We claim:

1. A controlled release oral formulation comprising about 400 to about 800 mg of flavoxate salt as an active ingredient and further comprising polyvinylpyrrolidone K30 (PVP K30) and/or colloidal silicon dioxide; wherein the formulation does not comprise an acidifying agent.

2. The controlled release oral formulation of claim 1, wherein the flavoxate salt is flavoxate hydrochloride.

3. The controlled release oral formulation of claim 1, further comprising one or more polymers selected from the group consisting of a methylcellulose, a polyvinyl alcohol, an acrylic copolymer, an ethylcellulose, and a hydroxypropylmethyl-cellulose (HPMC).

4. The controlled release oral formulation of claim 1, wherein the formulation further comprises one or more polymers, wherein the formulation comprises a ratio of polymers to flavoxate salt of about 1:8 to about 1:100.

5. The controlled release oral formulation of claim 1, wherein the formulation further comprises one or more binders, wherein the formulation comprises a ratio of binders to flavoxate salt of about 1:16.

6. The controlled release oral formulation of claim 5, wherein the one or more binders is dispersed in water, ethanol, acetonitrile, acetone, isopropyl alcohol, or a mixture thereof.

7. The controlled release oral formulation of claim 1, further comprising one or more excipients selected from the group consisting of magnesium stearate, talc, colloidal silicon dioxide, isopropyl alcohol, and lactose.

8. The controlled release oral formulation of claim 1, wherein the formulation is in a solid dosage form.

9. The controlled release oral formulation of claim 8, wherein the solid dosage form is a tablet having a thickness of about 6.20 mm to about 6.90 mm.

10. The controlled release oral formulation of claim 8, wherein the tablet has a hardness of about 6 kg/cm$^2$ to about 20 kg/cm$^2$.

11. The controlled release oral formulation of claim 9, wherein the tablet comprises micronized granules of the flavoxate salt of particle size with D90 of about 10 μm to about 100 μm.

12. The controlled release oral formulation of claim 1, wherein the formulation exhibits a pH-independent release profile of the flavoxate salt.

13. The controlled release oral formulation of claim 2, wherein the formulation releases flavoxate hydrochloride throughout a course of 12-24 hours.

14. The controlled release oral formulation of claim 1, wherein the formulation releases flavoxate salt over 24 hours, achieving a plasma concentration of flavoxate salt of 1 mcg/ml for 24 hours in a patient, wherein at least 10-15% of the flavoxate salt is released within the first hour, achieving a plasma concentration of flavoxate salt greater than or equal to 1 mcg/ml in the patient.

15. The controlled release oral formulation of claim 14, wherein the formulation achieves a plasma concentration of 3-methylflavone-8-carboxylic acid (MFCA) greater than or equal to 1 mcg/ml in the first to two and a half hours.

16. A formulation comprising about 400 mg to about 800 mg flavoxate salt as an active ingredient, HPMC K4M, and HPMC K15M, wherein the formulation further comprises PVP K30 and/or colloidal silicon dioxide and does not comprise an acidifying agent.

17. The formulation of claim 16, wherein the formulation comprises about 82% (w/w %) flavoxate salt.

18. The formulation of claim 16, wherein the flavoxate salt is flavoxate hydrochloride.

19. The formulation of claim 16, wherein the formulation comprises colloidal silicon dioxide.

20. The formulation of claim 16, wherein the formulation comprises about 0.5% to about 5% HPMC K4M, about 8% to about 15% HPMC K15M, about 0.5% to about 2% HPMC K100M, about 4% to about 6% PVP K30M, about 0.8% to about 1% magnesium stearate, up to about 1% colloidal silicon dioxide, and up to about 5% lactose, and optionally further comprises about 1% to about 3% talc.

21. The formulation of claim 16, wherein the formulation comprises about 0.5% to about 5% HPMC K4M, about 4% to about 15% HPMC K15M, about 0.5% to about 2% HPMC K100M, about 4% to about 6% PVP K30, about 0.5% to about 5% lactose, about 0.8% to about 1% magnesium stearate, and up to about 1 colloidal silicon dioxide, and optionally further comprises about 1% to about 3% talc.

22. The formulation of claim 16, comprising about 400 mg, about 600 mg, or about 800 mg flavoxate hydrochloride.

23. The formulation of claim 16, comprising about 800 mg flavoxate hydrochloride, about 19.5 mg HPMC K4M, about 58.5 mg HPMC K15M, about 8 mg HPMC K100M, about 48.5 mg PVP K30, about 10 mg magnesium stearate, about 25 mg lactose, and about 4 mg colloidal silicon dioxide.

24. The formulation of claim 16, comprising about 800 mg flavoxate hydrochloride, about 100 mg HPMC K15M, about 8 mg HPMC K100M, about 50 mg PVP K30, about 10 mg magnesium stearate, and about 4 mg colloidal silicon dioxide.

25. The formulation of claim 16, wherein the formulation releases flavoxate salt with a 12 hour to 24 hour release profile.

26. The formulation of claim 16, wherein the formulation exhibits a release profile of (a) 5-30% in 1 hour; (b) 45-85% in 8 hours, and (c) not less than 85% in 24 hrs.

27. The formulation of claim 16, wherein the formulation exhibits a pH-independent release profile.

28. The formulation of claim 16, wherein the formulation releases flavoxate salt over 24 hours, achieving a plasma concentration of flavoxate salt of 1 mcg/ml for 24 hours in a patient, wherein at least 10-15% of the flavoxate salt is released within the first hour, achieving a plasma concentration of flavoxate salt greater than or equal to 1 mcg/ml in the patient.

29. A method of treating at least one symptom of nocturia, dysuria, urgency, vesicle suprapubic pain, frequency, or urinary incontinence, associated with cystitis, prostatitis, urethritis, urethrocystitis, urethrotrigonitis, or symptoms of overactive bladder, wherein the method comprises administering the formulation of claim 1 to a patient in need thereof.

30. The controlled release oral formulation of claim 3, wherein the HPMC is chosen from the group consisting of HPMC K4M, HPMC K15M, and HPMC K100M.

* * * * *

UNITED STATES PATENT AND TRADEMARK OFFICE
CERTIFICATE OF CORRECTION

Page 1 of 1

PATENT NO. : 11,992,558 B2
APPLICATION NO. : 17/261858
DATED : May 28, 2024
INVENTOR(S) : Sushma Paul Berlia et al.

It is certified that error appears in the above-identified patent and that said Letters Patent is hereby corrected as shown below:

On the Title Page

Item (57), Lines 7-9, "The controlled release formulation of present invention may comprise micronized particles of drug." should read --The controlled release formulation of the present invention may comprise micronized particles of the drug.--.

Item (57), Line 11, "that is alcohol dose dumping risk-free" should read --that is free from risk of alcohol dose dumping--.

In the Claims

Claim 21, Column 30, Line 15, "up to about 1 colloidal silicon dioxide" should read --up to about 1 % colloidal silicon dioxide--.

Signed and Sealed this
Seventh Day of January, 2025

Derrick Brent
*Acting Director of the United States Patent and Trademark Office*